(12) United States Patent
Stadler et al.

(10) Patent No.: US 12,042,657 B2
(45) Date of Patent: Jul. 23, 2024

(54) ADAPTIVE CARDIAC RESYNCHRONIZATION THERAPY

(71) Applicant: Medtronic, Inc., Minneapolis, MN (US)

(72) Inventors: Robert W. Stadler, Shoreview, MN (US); Berthold Stegemann, Kassel (DE); Richard Cornelussen, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 764 days.

(21) Appl. No.: 17/115,050

(22) Filed: Dec. 8, 2020

(65) Prior Publication Data

US 2021/0085982 A1    Mar. 25, 2021

Related U.S. Application Data

(62) Division of application No. 15/928,773, filed on Mar. 22, 2018, now Pat. No. 10,881,861.
(Continued)

(51) Int. Cl.
*A61N 1/365* (2006.01)
*A61B 5/00* (2006.01)
(Continued)

(52) U.S. Cl.
CPC ........ *A61N 1/36578* (2013.01); *A61B 5/4836* (2013.01); *A61B 5/686* (2013.01);
(Continued)

(58) Field of Classification Search
CPC .... A61N 1/36578; A61B 5/4836; A61B 5/686
(Continued)

(56) References Cited

U.S. PATENT DOCUMENTS 4,955,376 A    9/1990  Callaghan et al.
5,117,824 A    6/1992  Keimel et al.
(Continued)

FOREIGN PATENT DOCUMENTS

WO    2015120466 A1    8/2015

OTHER PUBLICATIONS (PCT/US2019/012642) PCT Notification of Transmittal of the International Search Report and the Written Opinion of the International Searching Authority, mailed Apr. 10, 2019, 14 pages.
(Continued)

*Primary Examiner* — Nadia A Mahmood
(74) *Attorney, Agent, or Firm* — Shumaker & Sieffert, P.A.

(57) ABSTRACT

In some examples, a system can be used for delivering cardiac resynchronization therapy (CRT). The system may include a pacing device configured to be implanted within a patient. The pacing device can include a plurality of electrodes, signal generation circuitry configured to deliver ventricular pacing via the plurality of electrodes, and a sensor configured to produce a signal that indicates mechanical activity of the heart. Processing circuitry can be configured to identify one or more features of a cardiac contraction within the signal, and determine whether the contraction was a fusion beat based on the one or more features.

16 Claims, 15 Drawing Sheets

Related U.S. Application Data

(60) Provisional application No. 62/615,689, filed on Jan. 10, 2018.

(51) Int. Cl.
| | |
|---|---|
| *A61N 1/362* | (2006.01) |
| *A61N 1/39* | (2006.01) |
| *A61B 5/11* | (2006.01) |
| *A61B 5/35* | (2021.01) |
| *A61N 1/375* | (2006.01) |

(52) U.S. Cl.
CPC ......... *A61N 1/3621* (2013.01); *A61N 1/3624* (2013.01); *A61N 1/3627* (2013.01); *A61N 1/36507* (2013.01); *A61N 1/3987* (2013.01); *A61B 5/1102* (2013.01); *A61B 5/35* (2021.01); *A61N 1/3756* (2013.01); *A61N 1/39622* (2017.08)

(58) Field of Classification Search
USPC .......................................................... 607/25
See application file for complete search history.

(56) References Cited

U.S. PATENT DOCUMENTS

| | | | |
|---|---|---|---|
| 6,393,316 | B1 | 5/2002 | Gillberg et al. |
| 6,704,598 | B2 | 3/2004 | Ding et al. |
| 6,871,086 | B2 | 3/2005 | Nevo et al. |
| 6,871,096 | B2 | 3/2005 | Hill |
| 7,139,610 | B2 | 11/2006 | Ferek-Petric |
| 7,181,286 | B2 | 2/2007 | Sieracki et al. |
| 7,684,863 | B2 | 3/2010 | Parikh et al. |
| 8,145,308 | B2 | 3/2012 | Sambelashvili et al. |
| 8,521,268 | B2 | 8/2013 | Zhang et al. |
| 8,521,284 | B2 | 8/2013 | Kim et al. |
| 8,649,866 | B2 | 2/2014 | Brooke |
| 8,750,998 | B1 | 6/2014 | Ghosh et al. |
| 9,403,019 | B2 | 8/2016 | Sambelashvili et al. |
| 9,717,923 | B2 | 8/2017 | Thompson-Nauman et al. |
| 9,789,319 | B2 | 10/2017 | Sambelashvili |
| 2006/0155338 | A1 | 7/2006 | Mongeon et al. |
| 2009/0276001 | A1 | 11/2009 | Busacker et al. |
| 2009/0281590 | A1 | 11/2009 | Maskara et al. |
| 2010/0137935 | A1 | 6/2010 | Parikh et al. |
| 2010/0198291 | A1 | 8/2010 | Sambelashvili et al. |
| 2011/0319776 | A1* | 12/2011 | Sweeney ............... A61B 5/026 600/509 |
| 2012/0090627 | A1 | 4/2012 | Ransbury et al. |
| 2012/0109236 | A1 | 5/2012 | Jacobson et al. |
| 2013/0053906 | A1 | 2/2013 | Ghosh et al. |
| 2013/0197599 | A1 | 8/2013 | Sambelashvili et al. |
| 2014/0276928 | A1 | 9/2014 | Vanderpool et al. |
| 2014/0277245 | A1 | 9/2014 | Lu et al. |
| 2014/0330248 | A1 | 11/2014 | Thompson-Nauman et al. |
| 2014/0330287 | A1 | 11/2014 | Thompson-Nauman et al. |
| 2015/0142069 | A1 | 5/2015 | Sambelashvili |
| 2015/0142070 | A1 | 5/2015 | Sambelashvili |
| 2015/0224315 | A1 | 8/2015 | Stahmann |
| 2016/0175603 | A1 | 6/2016 | Sheldon et al. |
| 2016/0310031 | A1 | 10/2016 | Sarkar |
| 2017/0056649 | A1 | 3/2017 | Kane et al. |
| 2017/0291022 | A1 | 10/2017 | Shuros et al. |

OTHER PUBLICATIONS

U.S. Appl. No. 15/928,714, filed by Robert W. Stadler et al., filed Mar. 22, 2018.

U.S. Appl. No. 15/969,387, filed by Berthold Stegemann et al., filed May 2, 2018.

Szulik, et al., "Assessment of Apical Rocking: A New, Integrative Approach for Selection of Candidates for Cardiac Resynchronization Therapy," European Journal of Echocardiography, 2010, accessed on Dec. 20, 2017, pp. 663-869.

Mada, MD, "New Automatic Tools to Identify Responders to Cardiac Resynchronization Therapy," Journal of the American Society of Echocardiography, vol. 29, No. 10, Oct. 2016, pp. 966-972.

Stankovic, et al., "Relationship of Visually Assessed Apical Rocking and Septal Flash to Response and Long-term Survival Allowing Cardiac Resynchronization Therapy (PREDICT-CRT), " European Heart Journal, Cardiovascular Imaging, 2016, Accessed on Dec. 20, 2017, pp. 262-269.

First Office Action and Search Report, and translation thereof, from counterpart Chinese Application No. 201980007989.X dated Feb. 8, 2024, 23 pp.

* cited by examiner

ADAPTIVE CARDIAC RESYNCHRONIZATION THERAPY

This application claims the benefit of U.S. Provisional Patent Application Ser. No. 62/615,689, entitled, "ADAPTIVE CARDIAC RESYNCHRONIZATION THERAPY," and filed on Jan. 10, 2018, the entire content of which is incorporated by reference.

TECHNICAL FIELD

The disclosure relates to medical devices, and more particularly medical devices that monitor physiological conditions and deliver pacing therapy.

BACKGROUND

Some types of implantable medical devices, such as cardiac pacemakers or implantable cardioverter defibrillators, provide therapeutic electrical signals to a heart of a patient, such as bradycardia pacing, cardiac resynchronization therapy (CRT), anti-tachycardia pacing (ATP), and cardioversion/defibrillation shocks. The therapeutic electrical signals may be delivered to the heart in the form of pulses or shocks for pacing, cardioversion or defibrillation. In some cases, an implantable medical device may sense intrinsic depolarizations of the heart, and control the delivery of therapeutic signals to the heart based on the sensing.

CRT is one type of electrical stimulation therapy delivered by an implantable medical device. CRT may help enhance cardiac output by resynchronizing the electromechanical activity of the ventricles of the heart. Ventricular desynchrony may occur in patients that suffer from congestive heart failure (CHF). CRT includes delivering pacing stimuli to both ventricles (sometimes referred to as biventricular pacing), or to one ventricle (e.g., fusion pacing, such as left-ventricular pacing) with the intended result of a substantially simultaneous mechanical contraction and ejection of blood from the ventricles. Pacing may be delivered in the right ventricle (RV) and/or the left ventricle (LV) to restore ventricular synchrony.

Achieving a positive clinical benefit from CRT may be dependent on several therapy control parameters, such as the timing intervals used to control pacing pulse delivery to one or both ventricles, e.g., an atrio-ventricular (A-V) interval and/or an inter-ventricular (V-V) interval. The A-V interval controls the timing of ventricular pacing pulses relative to a preceding atrial event, e.g., an intrinsic or paced depolarization. The V-V interval controls the timing of a pacing pulse in one ventricle relative to a paced or intrinsic event in the other ventricle. Other therapy control parameters include a CRT pacing configuration, e.g., a fusion (single ventricle) configuration or a biventricular configuration, and a selection of electrodes used to deliver the ventricular pacing to a particular ventricle when more than one electrode is available and their polarities. In some cases, a lead may include multiple, e.g., four, electrodes from which one or more may be selected. In some cases, multiple electrodes may be selected as cathodes for a given chamber.

Medical device technology advancement has led toward smaller and smaller implantable devices. Recently, cardiac pacemakers have been introduced which can be implanted directly in a heart chamber. In some examples, such pacemakers may be leadless and delivered into the heart chamber using a catheter. Such miniaturized pacemakers may be referred to as intracardiac pacing devices (PDs), although they may be epicardially or extracardially implanted in some examples. An intracardiac PD may be configured to deliver CRT, e.g., as part of a system with one or more other devices.

SUMMARY

In general, this disclosure is directed to techniques for CRT. More particularly, this disclosure is directed to techniques for adapting CRT, e.g., controlling an A-V interval, V-V interval, or other therapy control parameter for CRT, based on an evaluation of the contraction following the CRT delivery. In some examples, the adaptation and contraction evaluation are performed, at least in part, by an intracardiac PD including a motion sensor that generates a signal that varies with cardiac contraction, e.g., one or more accelerometers. Based on the evaluation, processing circuitry may determine, for example, whether the contraction was a fusion beat.

A fusion beat is typically characterized by a wave complex formed by depolarization of the myocardium initiated by two different foci or sources, commonly a non-native stimulus from a PD and a native stimulus. A fusion beat happens when the depolarization from the different sources occur simultaneously (or nearly simultaneously) at the same region of the heart. There may be degrees of fusion, e.g., based on the degree of simultaneity, and a fusion beat as used herein may refer to a beat in which the degree of fusion was sufficient to be characterized as fusion, e.g., some metric of fusion was greater than a threshold.

In one example, a system for delivering cardiac resynchronization therapy comprises a pacing device configured for implantation within a patient. The pacing device comprises a plurality of electrodes, signal generation circuitry configured to deliver ventricular pacing via the plurality of electrodes, and a sensor configured to produce a signal that indicates mechanical activity of the heart. The system further comprises processing circuitry configured to identify one or more features of a cardiac contraction within the signal, determine whether the cardiac contraction is a fusion beat based on the one or more features, and control a timing interval for delivery of the ventricular pacing based on the determination.

Another example is a method for delivering cardiac resynchronization therapy by a pacing device. The method comprises, by processing circuitry of a medical device system comprising the pacing device, receiving a signal from a sensor of the pacing device, the signal indicating mechanical activity of a heart, identifying one or more features of a cardiac contraction within the signal, determining whether the cardiac contraction is a fusion beat based on the one or more features, and controlling a timing interval for delivery of ventricular pacing by the pacing device based on the determination.

Other examples include a system comprising means for receiving a signal from a sensor of the pacing device, the signal indicating mechanical activity of a heart, means for identifying one or more features of a cardiac contraction within the signal, means for determining whether the cardiac contraction is a fusion beat based on the one or more features, and means for controlling a timing interval for delivery of ventricular pacing by the pacing device based on the determination.

Other examples include a computer-readable storage medium comprising instructions that, when executed by processing circuitry of a medical device system, cause the processing circuitry to receive a signal from a sensor of the pacing device, the signal indicating mechanical activity of a heart, identify one or more features of a cardiac contraction within the signal, determine whether the cardiac contraction is a fusion beat based on the one or more features, and control a timing interval for delivery of ventricular pacing by the pacing device based on the determination.

Other examples include a system for delivering cardiac resynchronization therapy. The system comprises a pacing device configured for implantation within a patient. The pacing device comprises a plurality of electrodes, signal generation circuitry configured to deliver ventricular pacing via the plurality of electrodes to a left ventricle, a three-dimensional accelerometer configured to produce a signal that indicates mechanical activity of the heart, and a housing configured for implantation on or within the heart, wherein at the signal generation circuitry and the sensor are within the housing. The system further comprises processing circuitry configured to identify one or more features of a cardiac contraction within the signal, determine whether the cardiac contraction is a fusion beat based on the one or more features, and control a timing interval for delivery of the ventricular pacing based on the determination, wherein the timing interval comprises at least one of an A-V interval or a V-V interval, and wherein the one or more features of the cardiac contraction within the signal comprise an amount of motion in at least one direction other than the primary axis of motion during the cardiac contraction.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

Figure 1A:
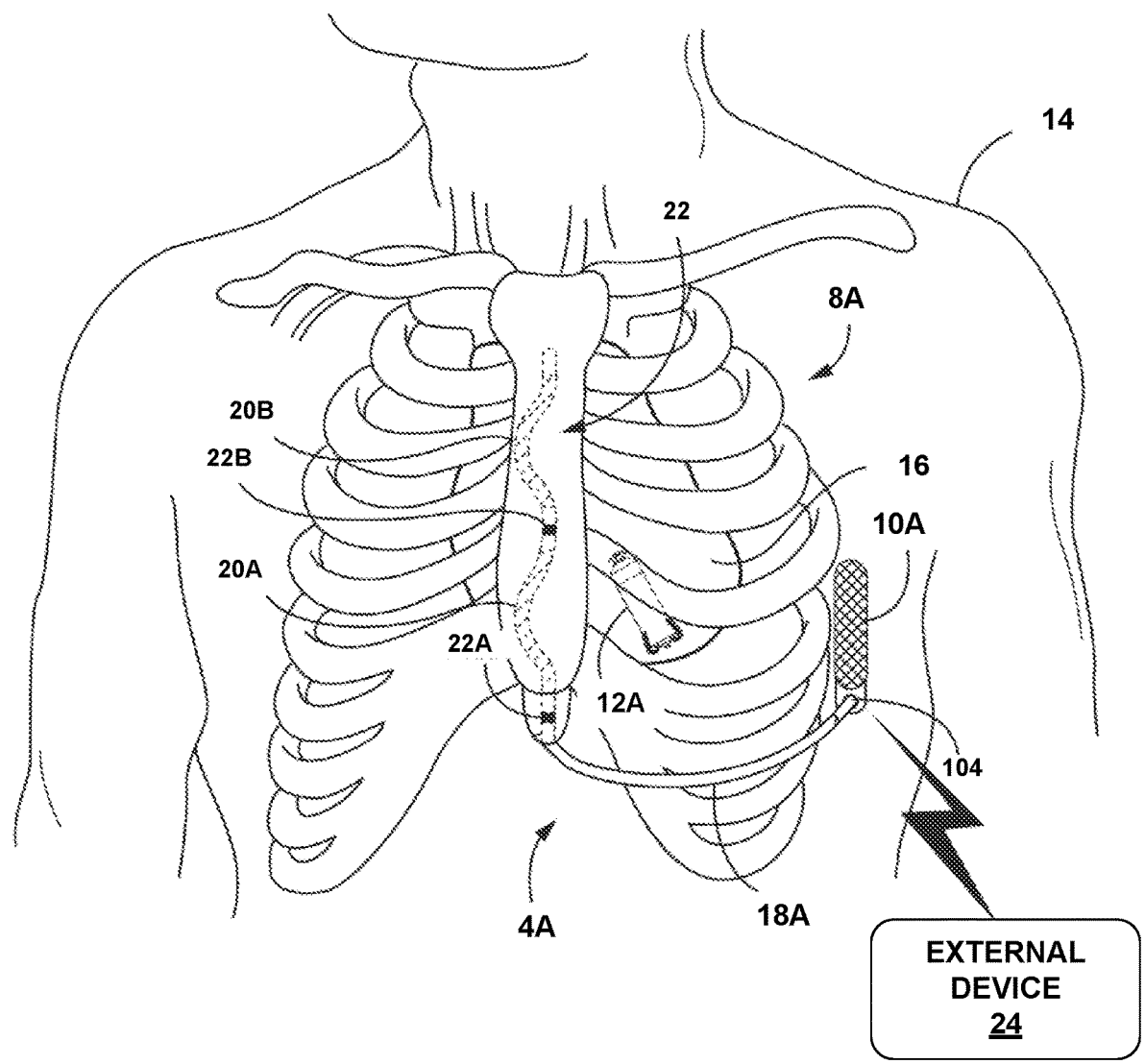
FIG. 1A is a conceptual diagram illustrating an example front view of a patient implanted with an example medical device system that includes an extracardiovascular ICD (EV-ICD) system and a pacing device (PD) that is implanted within a cardiac chamber of the patient in accordance with one or more aspects of this disclosure.

In general, this disclosure describes example techniques related to delivery of CRT to a patient, e.g., using an intracardiac PD. The introduction of such PDs, and the resulting elimination of the need for transvenous intracardiac leads, provides several advantages. For example, complications due to infection associated with a lead extending from a subcutaneous pacemaker pocket transvenously into the heart can be eliminated. Other complications, such as "twiddler's syndrome," lead fracture, or poor connection of the lead to the pacemaker are eliminated in the use of an intracardiac PD.

In some examples, a ventricular PD may be unable to detect atrial depolarizations. In some examples, another implantable medical device (IMD) detects atrial depolarizations. The other IMD may send signals to the ventricular PD. The signals may indicate the timing of atrial depolarizations, or may be a trigger to deliver a ventricular pacing pulse.

One or both of the ventricular PD or the other IMD may maintain timing intervals that control the timing of ventricular pacing pulses for CRT relative to atrial events, such as paced or intrinsic depolarizations. According to some example techniques for delivering CRT, a memory, e.g., of a ventricular PD that delivers CRT, another IMD, and/or an external computing device, stores one or more values of one or more intervals between an atrial event and a ventricular event, e.g., an A-V interval, determined for the patient. An atrial or ventricular event may be a depolarization or contraction, as examples, but may be any fiducial marker in an EGM or other signal that varies with cardiac electrical or mechanical activity. In some examples, the ventricular event is a sensed or intrinsic ventricular event, and the interval is an A-$V_s$ interval. In some examples, the memory stores values for both of an interval between a sensed atrial event and the ventricular event, e.g., an $A_s$-$V_s$ interval, and an interval between a paced atrial event and the ventricular event, e.g., an $A_p$-$V_s$ interval. The values stored for the patient in the memory may be determined by monitoring the A-V conduction of the patient prior to, or during a suspension of, delivery of CRT.

Processing circuitry, e.g., of the ventricular PD, the other IMD, and/or the external computing device, may control the delivery of CRT based on a selected value of the A-V interval. For example, the processing circuitry may determine whether to control a ventricular PD to deliver fusion pacing in which only one ventricle is paced in coordination with the other ventricle's intrinsic activation, e.g., left-ventricular pacing, or two PDs to deliver biventricular pacing to the patient based on the selected A-V interval value. In examples in which the A-V interval value selected based on the heart rate is an A-$V_s$ interval value, the processing circuitry may further determine, based on the selected A-$V_s$ value, an A-$V_p$ interval value for timing the delivery of the fusion or biventricular pacing. Additionally, or alternatively, a PD or other IMD may similarly maintain and utilize V-V intervals that control the timing of ventricular pacing pulses for CRT in one ventricle relative to ventricular events in another ventricle, such as paced or intrinsic depolarizations of the other ventricle.

CRT may be made more effective for a given patient by determining patient specific values of CRT control parameters, such as A-V and/or V-V interval values. Effective CRT for a given patient may be maintained by periodically updating to determine parameter CRT control values. Left ventricular hemodynamic variables, blood pressure measures, or echocardiography have been used to determine and/or update CRT control parameter values for a patient. However, such metrics are not readily evaluated in a closed loop manner by the implantable medical device that delivers the CRT.

According to some techniques for adapting delivery of CRT, the stored A-V or V-V interval values may be validated and, if necessary, updated periodically, by suspending the delivery of CRT, and measuring a current value of the A-V or V-V interval (representative of the current intrinsic A-V conduction) while delivery of CRT is suspended. Suspending the delivery of CRT may refer to, as examples, withholding ventricular pacing for one or more cardiac cycles, increasing an A-$V_p$ delay sufficiently so that intrinsic A-V conduction may be observed, or pacing one ventricle at a sufficiently long A-$V_p$ delay and measuring intrinsic conduction on the other ventricle. The stored value of the A-V or V-V interval may be updated if the currently measured value of the interval to is not sufficiently similar to the stored value, e.g., by replacing the stored A-V or V-V interval value with the currently measured value.

In addition to periodic adjustment of A-V and/or V-V intervals based on observation of intrinsic conduction, some medical devices may be configured to automatically switch the pacing configuration, e.g., from a fusion pacing configuration to a biventricular pacing configuration (or vice versa), based on periodic intrinsic conduction observations. For example, medical devices configured to provide AdaptivCRT™, available from Medtronic plc of Dublin, Ireland, are configured to both automatically change CRT control intervals and CRT pacing configuration based on periodic observations of intrinsic conduction to achieve more efficient physiologic pacing and to improve hemodynamics of the patient. Fusion pacing and biventricular pacing are described in further detail below. While the pacing stimuli may be pacing pulses or continuous time signals, the pacing stimuli are primarily referred to herein as pacing pulses for ease of description. An example of the AdaptivCRT™ algorithm is described in U.S. Pat. No. 9,403,019 to Sambelashvili et al., which is entitled, "ADAPTIVE CARDIAC RESYNCHRONIZATION THERAPY," and issued on Aug. 2, 2016. U.S. Pat. No. 9,403,019 to Sambelashvili et al. is incorporated herein by reference in its entirety. Another example of AdaptivCRT™ is described in U.S. Pat. No. 9,789,319 to Sambelashvili, which is entitled, "SYSTEMS AND METHODS FOR LEADLESS CARDIAC RESYNCHRONIZATION THERAPY," and issued on Oct. 17, 2017. U.S. Pat. No. 9,789,319 to Sambelashvili is incorporated herein by reference in its entirety.

Fusion-based CRT (also referred to herein as fusion pacing) may be useful for restoring a depolarization sequence of a heart of a patient, which may be irregular due to ventricular dysfunction, in patients with preserved intrinsic atrial-ventricular (AV) conduction. In a fusion pacing configuration, a medical device delivers one or more fusion pacing pulses to one of the ventricles, and not the other. The medical device delivers the one or more fusion pacing pulses to a later-contracting ventricle (V2) to pre-excite the V2 and synchronize the depolarization of the V2 with the depolarization of the earlier contracting ventricle (V1). The paced ventricular activation of the V2 may "fuse" (or "merge") with the ventricular activation of the V1 that is attributable to intrinsic conduction of the heart. In this way, the intrinsic and pacing-induced excitation wave fronts may fuse together such that the depolarization of the V2 is resynchronized with the depolarization of the V1.

The medical device may be configured to deliver the fusion pacing pulse to the V2 according to a fusion pacing interval, which indicates the time relative to an atrial pace or sense event at which the fusion pacing pulse should be delivered to the V2. An atrial sense event may be, for example, a P wave of a sensed electrical cardiac signal and an atrial pacing event may be, for example, the time at which a stimulus is delivered to the atrium.

In some examples, the right ventricle (RV) may be the V1 and the left ventricle (LV) may be the V2. In other examples, the LV may be the V1 while the RV may be the V2. While the disclosure primarily refers to examples in which the first depolarizing ventricle V1 is the RV and the later depolarizing ventricle V2 is the LV, the devices, systems, techniques described herein for providing CRT may also apply to examples in which the first depolarizing ventricle V1 is the LV and the later depolarizing ventricle V2 is the RV.

In some fusion pacing techniques, a pacing pulse to the V2 ($V2_P$) is delivered upon expiration of a fusion pacing interval that is determined based on the intrinsic depolarization of the V1, which may be indicated by a sensing of ventricular activation ($V1_S$). Ventricular activation may be indicated by, for example, an R-wave of a sensed electrical cardiac signal. An example of a fusion pacing technique that times the delivery of the V2 pacing pulse ($V2_P$) to the intrinsic depolarization of the V1 is described in U.S. Pat. No. 7,181,286 to Burnes et al., which is entitled, "APPARATUS AND METHODS OF ENERGY EFFICIENT, ATRIAL-BASED BI-VENTRICULAR FUSION-PACING," and issued on Feb. 20, 2007. U.S. Pat. No. 7,181,286 to Burnes et al. is incorporated herein by reference in its entirety.

In one example disclosed by U.S. Pat No. 7,181,286 to Burnes et al., a pacing pulse to the V2 ($V2_P$) is delivered a predetermined period following an atrial pace or sense event ($A_{P/S}$), where the predetermined period is substantially equal to the duration of time between the atrial pace or sense event ($A_{P/S}$) and a V1 sensing event ($V1_S$) of at least one prior cardiac cycle decremented by a duration of time referred to as the pre-excitation interval (PEI). Thus, one example equation that may be used to determine a fusion pacing interval ($A_{P/S}$–$V2_P$):

$$A_{P/S}-V2_P=(A_{P/S}-V1_S)-\text{PEI} \quad\quad \text{Equation (1)}$$

A cardiac cycle may include, for example, the time between the beginning of one heart beat to the next heartbeat. The duration of time between the atrial pace or sense event ($A_{P/S}$) and a V1 sensing event ($V1_S$) may be, for example, a measurement of intrinsic AV conduction time from an atrium to the first contracting ventricle of the heart of the patient. The PEI may indicate the amount of time with which a V2 pacing pulse precedes a V1 sensing event to achieve the fusing of the electromechanical performance of the V1 and V2. That is, the PEI may indicate the amount of time from the delivery of the V2 pacing pulse that is required to pre-excite the V2, such that the electromechanical performance of V1 and V2 merge into a fusion event. In some examples, the PEI is automatically determined by a medical device delivering the pacing therapy, e.g., based on determined intrinsic conduction times, while in other examples, the PEI may be predetermined by a clinician. In some examples, the PEI is a programmed value (e.g., about one millisecond (ms) to about 250 ms or more, such as about 100 ms to about 200 ms, or about 10 ms to about 40 ms) or is an adaptive value, such as about 10% of a measured intrinsic A-V2 conduction interval or measured intrinsic A-A cycle length.

The magnitude of the PEI may differ based on various factors, such as the heart rate of the patient, a dynamic physiologic conduction status of the heart of the patient, which may change based upon the physiological condition of the patient (e.g., ischemia status, myocardial infarction status, and so forth), as well as factors related to the therapy system, such as the location of sensing electrodes of the therapy system, the location of the pacing electrodes of the therapy system, and internal circuitry processing delays of the medical device.

Another technique for determining the timing of the delivery of a pacing pulse to a later depolarizing ventricle (V2) (which is sometimes also referred to as a "fusion pacing interval") is described in U.S. Patent Application Publication No. 2010/0198291 by Sambelashvili et al., which is incorporated herein by reference in its entirety. In some examples described by U.S. Patent Application Publication No. 2010/0198291 by Sambelashvili et al., the timing of the delivery of a pacing pulse is based on a depolarization of the V2 in at least one prior cardiac cycle. The depolarization of the V2 may be detected by sensing an event in the V2 ($V2_S$), such as an R-wave of an electrical cardiac signal. The V2 pacing pulse ($V2_P$) is timed such that an evoked depolarization of the V2 is affected in fusion with the intrinsic depolarization of the first depolarizing ventricle (V1), resulting in a ventricular resynchronization. In this way, the V2 pacing pulse ($V2_P$) may pre-excite the conduction delayed V2 and help fuse the activation of the V2 with the activation of the V1 from intrinsic conduction. The interval of time between the V2 pacing pulse ($V2_P$) and the V2 sensing event ($V2_S$) of the same cardiac cycle may be referred to as the adjusted PEI.

In some examples disclosed by U.S. Patent Application Publication No. 2010/0198291 by Sambelashvili et al., the predetermined period at which an IMD delivers the V2 pacing pulse ($V2_P$) following an atrial pace or sense event ($A_{P/S}$) is substantially equal to the duration of time between an atrial event (sensed or paced) ($A_{P/S}$) and a V2 sensing event ($V2_S$) of at least one prior cardiac cycle decremented by a duration of time referred to as an adjusted PEI. That is, in some examples, the adjusted PEI indicates the desired interval of time between the delivery of the V2 pacing pulse ($V2_P$) and the V2 sensing event ($V2_S$) of the same cardiac cycle. One example equation that may be used to determine the timing of a fusion pacing pulse using a technique described by U.S. Patent Application Publication No. 2010/0198291 by Sambelashvili et al. is:

$$A_{P/S}-V2_P=(A_{P/S}-V2_S)-\text{adjusted PEI} \quad\quad \text{Equation (2)}$$

The duration of time between an atrial pace or sense event ($A_{P/S}$) and a V2 sensing event ($V2_S$) may be referred to as an atrioventricular (A-V) interval or delay. The adjusted PEI may indicate an interval of time prior to a V2 sensing event ($V2_S$) at which it may be desirable to deliver the V2 pacing pulse ($V2_P$) to pre-excite the V2 and merge the electromechanical performance of V2 and V1 into a fusion event. In some examples described by U.S. Patent Application Publication No. 2010/0198291 by Sambelashvili et al., an adjusted PEI is a linear function that is based on V1 sensing event ($V1_S$) and a V2 sensing event ($V2_S$) of the same cardiac cycle, based on the time between an atrial pace or sense event ($A_{P/S}$) and a V2 sensing event, or any combination thereof.

As an example, adjusted PEI may be determined as follows:

$$\text{Adjusted PEI}=a(V1_S-V2_S)+b \quad\quad \text{Equation (3)}$$

According to U.S. Patent Application Publication No. 2010/0198291 by Sambelashvili et al., in Equation (3), the coefficients "a" and "b" may be fixed, empiric coefficients that are selected by a clinician or determined based on an adjusted PEI value selected by a clinician. In some examples, the coefficient "a" in Equation (3) may be about 1 and the coefficient "b" may be substantially equal to the PEI. In this case, the adjusted PEI is substantially equal to a time interval between a V1 sensing event ($V1_S$) and a V2 sensing event ($V2_S$) of the same cardiac cycle, incremented by the PEI. As a result, the $A_{P/S}$–$V2_P$ interval for timing the delivery of a V2 pacing pulse may be determined as follows:

$$A_{P/S}-V2_P=(A_{P/S}-V2_S)-[(V1_S-V2_S)+\text{PEI})] \quad\quad \text{Equation (4)}$$

Other values for the "a" and "b" coefficients in Equation (3) may be selected. In addition, other types of fusion pacing configurations may also be used in accordance with the techniques described herein. For example, other fusion pacing intervals described by U.S. Pat. No. 7,181,286 to Burnes et al. and U.S. Patent Application Publication No. 2010/0198291 by Sambelashvili et al. can also be used to control fusion pacing in accordance with techniques described herein. An example of CRT is described in U.S. Pat. No. 6,871,096 to Hill, which is entitled "SYSTEM AND METHOD FOR BI-VENTRICULAR FUSION PACING" and is incorporated herein by reference in its entirety.

In some examples, fusion pacing is implemented as left-ventricular pacing. Most left-ventricular pacing is via a lead introduced into the coronary sinus such that the electrodes are located proximate the left-ventricular free wall. Left intra-cardiac, endocardial stimulation has been proposed to improve left ventricular electrical activation, e.g., relative to pacing using a coronary sinus lead. The high electrical conduction velocity of the endocardium allows for a faster, more homogenous activation of the myocardium. At the same time, the optimal stimulation location of the left ventricular stimulation site may become less important than with electrodes on a coronary sinus lead. An intracardiac PD implanted within the left ventricle may be configured to provide intra-cardiac, endocardial stimulation. In other examples, an extracardiac PD may be coupled to electrodes on a lead that are positioned to provide intra-cardiac, endocardial stimulation.

In contrast to fusion pacing, in a biventricular pacing configuration, one or more medical devices, e.g., including at least one intracardiac PD, may deliver pacing pulses to both the LV and the RV to resynchronize the contraction of the LV and RV. In a biventricular pacing configuration, the medical device(s) may deliver stimulation to coordinate contraction of the LV and the RV, even in the absence of intrinsic AV conduction of the heart.

In some proposed pacing techniques for adapting CRT, such as AdaptivCRT™, a pacing configuration (e.g., fusion pacing or biventricular pacing) and timing of the pacing pulses (e.g., a fusion pacing interval, such as a $A_{P/S}-V2_P$ interval, or biventricular pacing intervals, such as an $A_{P/S}-V1_P$ and $A_{P/S}-V2_P$ intervals, or an $A_{P/S}-V1_P$ and $V1_P-V2_P$ intervals) are periodically adjusted based on periodic intrinsic conduction measurements to achieve more efficient physiologic pacing and optimal hemodynamics. For example, some proposed cardiac rhythm management medical device systems are configured to deliver CRT by delivering pacing to a heart of a patient in accordance with a fusion pacing configuration and, if loss of intrinsic AV conduction is detected (e.g., AV block), switching to a biventricular pacing configuration. Thus, a medical device system configured to adapt CRT, e.g., to perform the AdaptivCRT™ algorithm, may be configured to switch from a fusion pacing configuration to a biventricular pacing configuration in response to determining a heart of a patient is no longer intrinsically conducting.

In some existing proposed techniques, a medical device system switches from a fusion pacing configuration to a biventricular pacing configuration if the loss of intrinsic AV conduction is detected based on a measurement of intrinsic conduction time, which may be performed as part of the A-V interval determination. For example, loss of intrinsic AV conduction may be detected if a measured A-V1 conduction time ($A_{P/S}-V1_S$) is greater than (or greater than or equal to in some examples) a predetermined threshold value. In some examples, the predetermined threshold value is selected based on previous intrinsic conduction time intervals (e.g., may be a percentage of a mean or median of a certain number of prior intrinsic conduction time measurements). In other examples, the predetermined threshold value may be selected by a clinician to be, for example, a value that indicates the depolarization time of V1 that results in maintenance of ventricular synchrony or cardiac output at a desirable level.

To measure intrinsic conduction time, the CRT pacing may be suspended to allow the heart of the patient to conduct in the absence of cardiac rhythm management therapy and to avoid interference between the delivery of pacing pulses and sensing of ventricular activation. In some examples, if pacing is delivered to an atrium of the heart, such pacing may be maintained, while pacing to the ventricles may be suspended. The measurement of intrinsic conduction time may be determined, e.g., as the time between an atrial pace or sense event ($A_{P/S}$) and a V1 sensing event ($V1_S$), which may be referred to generally as an $A-V_S$ interval. In such examples, the determinations of the intrinsic conduction time measurements may take place, for example, once a minute, once an hour, or once every 24 hours, although other frequencies may also be used.

The determinations of intrinsic conduction time may involve the suspension of some or all pacing therapy to the heart of the patient for at least one cardiac cycle, which may reduce the amount of synchronization of the ventricles of the heart during at least that one cardiac cycle. Furthermore, determinations of intrinsic conduction time, being based on electrical intra-cardiac conduction, may not account for cardiac tissue properties, such as myocardial stiffness and contractile properties. As described herein, the devices, systems, and techniques for providing CRT are directed to adapting CRT control parameters, such as timing intervals and pacing configuration, while lessening or eliminating the need to suspend the delivery of electrical stimulation to the heart of the patient and the reliance on electrical conduction measurements.

Further, a ventricular PD may have difficulty delivering CRT by itself. For example, a ventricular PD may have difficulty sensing a paced or intrinsic atrial depolarization from which to time the delivery of its ventricular pacing pulse, e.g., due to the relatively small distance between its electrodes. A ventricular PD may, for similar reasons, have difficulty detecting whether its pacing pulses captured the ventricle. Certain existing techniques for evaluating whether ventricular pacing pulses for CRT captured the ventricle as intended utilize a far-field EGM to detect capture. Additionally, algorithms for adapting the timing parameters of CRT, such as those described above, typically use a far-field electrogram (EGM) to detect intrinsic AV conduction during suspension of CRT. A far-field EGM may not be obtainable a ventricular PD due to the relatively small distance between its electrodes.

Figure 1B:
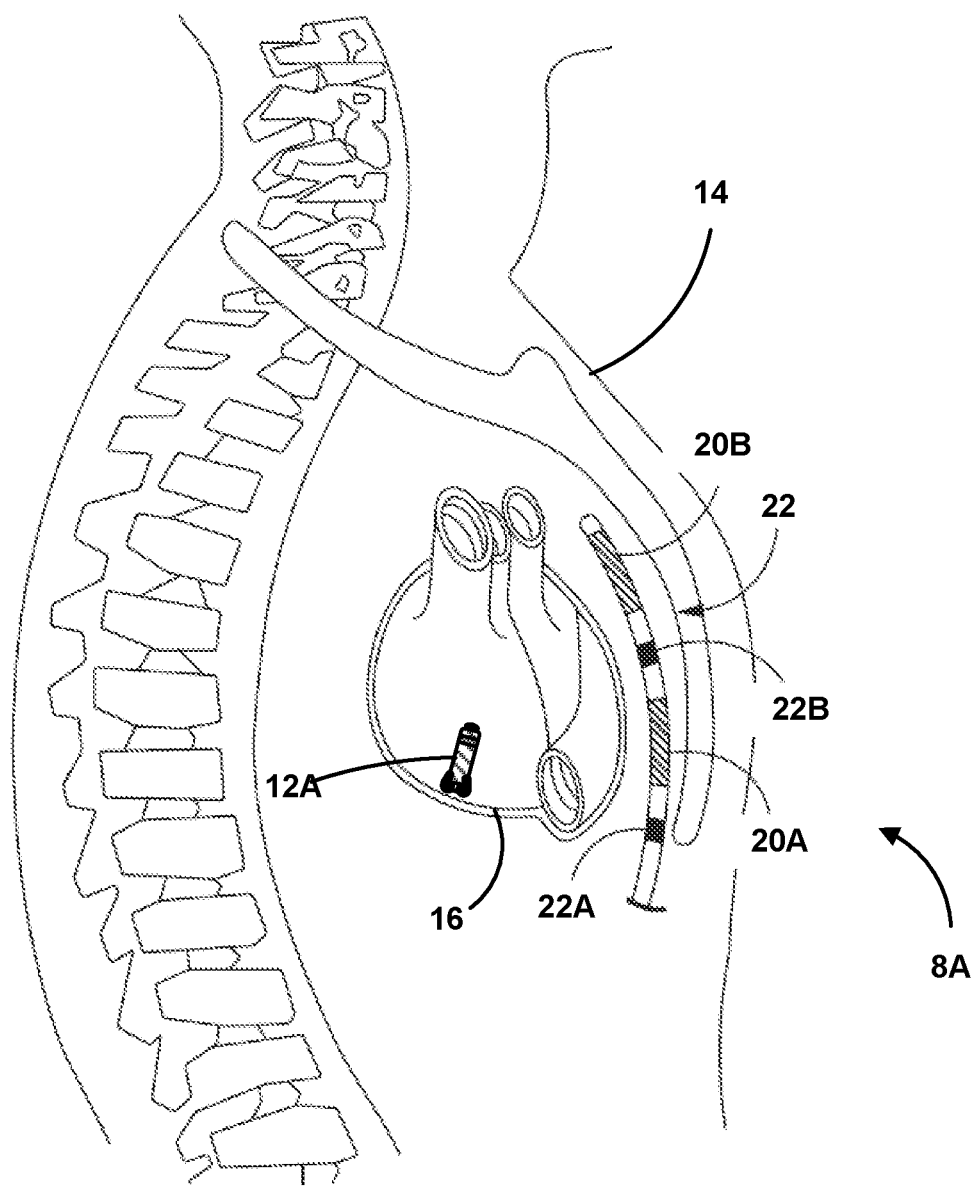
FIG. 1B is a conceptual diagram illustrating an example side view of a patient implanted with the example medical device system of FIG. 1A, in accordance with one or more aspects of this disclosure.
Figure 1C:
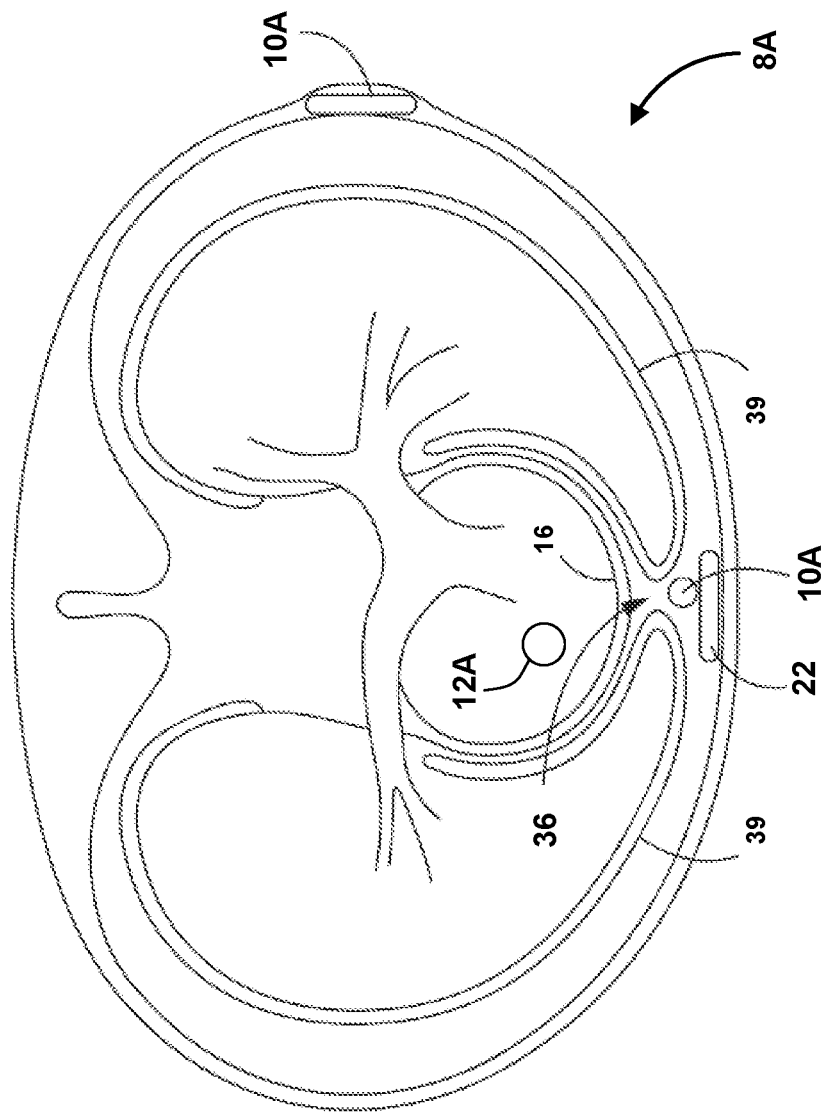
FIG. 1C is a conceptual diagram illustrating an example transverse view of a patient implanted with the example medical device system of FIG. 1A, in accordance with one or more aspects of this disclosure.

FIGS. 1A-1C are conceptual diagrams illustrating various views of an example cardiac medical device system 8A implanted within a patient 14. Components with like numbers in FIGS. 1A-1C may be similarly configured and may provide similar functionality. Medical device system 8A as illustrated in FIGS. 1A-1C may be configured to perform one or more of the techniques described herein with respect to evaluating and adapting CRT.

FIG. 1A is a conceptual diagram illustrating is an example front view of a patient implanted with an example cardiac medical device system 8A that includes an extracardiovascular implantable cardioverter defibrillator (ICD) system 4A, and a pacing device (PD) 12A that is implanted within a cardiac chamber of patient 14 in accordance with one or more aspects of this disclosure. PD 12A may be, for example, an implantable leadless pacing device (e.g., a pacemaker, cardioverter, and/or defibrillator) that provides electrical signals to heart 16A via electrodes carried on the housing of PD 12A.

With respect to FIGS. 1A-1C, and elsewhere herein, PD 12A is generally described as being attached within a chamber of heart 16A. That is, PD 12A is described in various portions of this disclosure as an intracardiac pacing device. In other examples that are consistent with aspects of this disclosure, PD 12A may be attached to an external surface of heart 16A, such that PD 12A is disposed outside of heart 16A but can pace a desired chamber. In one example, PD 12A is attached to an external surface of heart 16A, and one or more components of PD 12A may be in contact with the epicardium of heart 16A. Although PD 12A is generally described as a pacing device for intracardiac implantation, PD 12A may alternatively be configured to attach to an external surface of heart 16A and operate as an extracardiac pacing device.

In one example, PD 12A can be implanted within left ventricle of a heart to sense electrical activity of heart and/or deliver electrical stimulation, e.g., CRT such as fusion pacing, to heart. Fusion pacing may involve LV only pacing with PD 12 in coordination with the intrinsic RV activation. Alternatively, fusion pacing can involve pacing the RV with PD 12 in coordination with the intrinsic LV activation. In this scenario, PD 12 is placed on or within the right ventricle.

PD 12A is schematically shown in FIG. 1A attached to a wall of the left ventricle via one or more fixation elements (e.g. tines, helix, etc.) that penetrate the tissue. These fixation elements may secure PD 12A to the cardiac tissue and retain an electrode (e.g., a cathode or an anode) in contact with the cardiac tissue. PD 12A (and PD 12B in FIG. 2) may be implanted at or proximate to the apex of the heart. In other examples, a PD may be implanted at other left-ventricular locations, e.g., on the free-wall or septum.

PD 12A may also include one or more motion sensors (e.g., accelerometers, gyroscopes, or electrical or magnetic field sensors) configured to detect and/or confirm cardiac conditions (e.g., ventricular dyssynchrony or tachyarrhythmias) from these mechanical motions of heart 16. The mechanical motions of the heart detected using such sensors may also be used to evaluate contractions during CRT according to the techniques described herein. In examples in which PD 12A is implanted at or near the apex of heart 16, the motion sensor may correspondingly be located at or near the apex. Since PD 12A includes two or more electrodes carried on the exterior housing of PD 12A, no other leads or structures need to reside in other chambers of heart 16. However, in other examples, medical device system 8A may include additional PDs within respective chambers of heart 16 (e.g., left atrium, right atrium), or coupled by leads to electrodes in such chambers of heart.

ICD system 4A includes ICD 10A that is connected to at least one implantable cardiac defibrillation lead 18A (hereinafter, "defibrillation lead 18A"). ICD 10A is configured to deliver high-energy cardioversion shocks or defibrillation pulses to heart 16A of patient 14, in response to atrial fibrillation or ventricular fibrillation being detected. Cardioversion shocks are typically delivered in synchrony with a detected R-wave, when fibrillation detection criteria are met. Defibrillation pulses are typically delivered when fibrillation criteria are met, and the R-wave cannot be discerned from signals sensed by ICD 10A.

ICD 10A of FIG. 1A may be implanted subcutaneously or submuscularly on the left side of patient 14 above the ribcage. FIG. 1C is a conceptual diagram illustrating an example transverse view of a patient implanted with the example medical device system of FIG. 1A, in accordance with one or more aspects of this disclosure. Defibrillation lead 18A of FIG. 1A may be implanted at least partially in a substernal location in FIG. 1A, e.g., between the ribcage and/or sternum 22 and heart. In one such configuration, a proximal portion of defibrillation lead 18A extends subcutaneously from ICD 10A toward the sternum, and a distal portion of lead 18A extends under or below the sternum 22 in the anterior mediastinum 36 (see FIG. 1C). The anterior mediastinum 36 is bounded laterally by the pleurae 39 (see FIG. 1C), posteriorly by the pericardium, and anteriorly by the sternum 22. In some instances, the anterior wall of the anterior mediastinum 36 may also be formed by the transversus thoracis and one or more costal cartilages. The anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of defibrillation lead 18A extends along the posterior side of the sternum 22 substantially within the loose connective tissue and/or substernal musculature of anterior mediastinum 36. Defibrillation lead 18A may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 16A and not above the sternum 22 or ribcage.

In other examples, defibrillation lead 18A may be implanted at other extracardiovascular locations. For example, defibrillation lead 18A may extend subcutaneously above the ribcage from ICD 10A toward a center of the torso of patient 14, bend or turn near the center of the torso, and extend subcutaneously superior above the ribcage and/or sternum 22, like that shown in FIG. 1A. Defibrillation lead 18A may be offset laterally to the left or the right of the sternum 22 or located over the sternum 22. Defibrillation lead 18A may extend substantially parallel to the sternum 22 or be angled lateral from the sternum 22 at either the proximal or distal end. In another example, defibrillation lead 18A and/or a pacing lead or sensing lead may be implanted within the pericardial sac of heart 16A, within the pericardium of heart 16A, epicardially with respect to heart 16A, or at another location.

Defibrillation lead 18A of FIG. 1A may include an insulative lead body having a proximal end that includes a connector configured to be connected to ICD 10A and a distal portion that includes one or more electrodes. Defibrillation lead 18A may also include one or more conductors that form an electrically conductive path within the lead body and interconnect the electrical connector and respective ones of the electrodes.

Defibrillation lead 18A of FIG. 1A includes a defibrillation electrode that, in the illustrated example, includes two sections or segments 20A and 20B. Segments 20A and 20B are collectively (or alternatively) referred to herein as "defibrillation electrodes 20." Defibrillation electrodes 20 of FIG. 1A are positioned toward the distal portion of defibrillation lead 18A, e.g., toward the portion of defibrillation lead 18A extending along sternum 22 of patient 14. Defibrillation lead 18A of FIG. 1A is placed below and/or along sternum 22 such that a therapy vector between defibrillation electrodes 20A or 20B and a housing electrode formed by ICD 10A or on ICD 10A (or other second electrode of the therapy vector) is substantially across a ventricle of heart 16A. The therapy vector may, in one example, be viewed as a line that extends from a point on defibrillation electrodes 20 (e.g., a center of one of the defibrillation electrode sections 20A or 20B) to a point on the housing electrode of ICD 10A. Each of defibrillation electrodes 20 of FIG. 1A may, in one example, be an elongated coil electrode. In some examples, a defibrillation lead may include more or fewer than the two defibrillation electrodes 20 in the illustrated example of defibrillation lead 18A, such as a single coil defibrillation electrode 20.

FIG. 1B is a conceptual diagram illustrating an example side view of a patient implanted with the example medical device system of FIG. 1A, in accordance with one or more aspects of this disclosure. Defibrillation lead 18A may also include one or more sensing electrodes, such as sensing electrodes 22A and 22B, located along the distal portion of defibrillation lead 18A. In the example illustrated in FIGS. 1A and 1B, sensing electrodes 22A and 22B are separated from one another by defibrillation electrode 20A. In other examples, however, sensing electrodes 22A and 22B may be both distal of defibrillation electrodes 20, or both proximal of defibrillation electrodes 20. In other examples, defibrillation lead 18A may include a greater number or a fewer number of electrodes at various locations proximal and/or distal to defibrillation electrodes 20. In these and/or other examples, ICD 10A may include one or more electrodes on another lead (not shown in FIGS. 1A-1C).

ICD system 4A may sense electrical signals via one or more sensing vectors that include combinations of electrodes 22A and 22B and the housing electrode of ICD 10A. For example, ICD 10A may obtain electrical signals that are sensed using a sensing vector between sensing electrodes 22A and 22B, obtain electrical signals sensed using a sensing vector between sensing electrode 22B and the conductive housing electrode of ICD 10A, obtain electrical signals sensed using a sensing vector between sensing electrode 22A and the conductive housing electrode of ICD 10A, or a combination thereof. In some instances, ICD 10A may sense cardiac electrical signals using a sensing vector that includes one of the defibrillation electrode sections 20A and 20B and one of sensing electrodes 22A and 22B or the housing electrode of ICD 10A.

The sensed electrical intrinsic signals include electrical signals that are generated by cardiac muscle and are indicative of depolarizations and repolarizations of heart 16A at various times during the cardiac cycle. Moreover, the sensed electrical intrinsic signals may be indicative of one or more cardiac events with respect to the functioning of heart 16A. The sensed electrical signals may also include electrical signals, e.g., pacing pulses, generated by PD 12A and delivered to heart 16A. ICD 10A analyzes the electrical signals sensed by the one or more sensing vectors to detect tachyarrhythmia, such as atrial tachycardia, atrial fibrillation, ventricular tachycardia, or ventricular fibrillation. In response to detecting the tachyarrhythmia, e.g., a ventricular fibrillation, ICD 10A may begin to charge a storage element, such as a bank of one or more capacitors. Upon determining that the storage element is sufficiently charged, ICD 10A may deliver one or more defibrillation pulses to certain chamber(s) of heart 16A via defibrillation electrodes 20 of defibrillation lead 18A, if ICD 10A determines that the tachyarrhythmia is still present.

In the example of FIG. 1A, PD 12A is implanted within the left ventricle of heart 16A, to provide pacing pulses to the left ventricle, e.g., for CRT. While illustrated as being implanted within the left ventricle as an example, it will be appreciated that PD 12A may be implanted at different positions as well. For instance, PD 12A may be implanted epicardially. That is, in accordance with epicardial implantation, PD 12A may be positioned externally to heart 16A and may be connected via one or more leads or in a leadless fashion to the left ventricle of heart 16A. In other examples, PD 12A or other PDs may be implanted within or externally to other chambers of heart 16A

PD 12A may be constructed to have dimensions to fit within the available volume of the left ventricle of heart 16A and to be attachable to a wall, e.g., at or near the apex, of the left ventricle of heart 16A. A smaller size of PD 12A may also reduce the risk of thrombus forming in heart 16A. In some examples, PD 12A may leverage EGM sensing capabilities of ICD 10A, and therefore, may not include EGM sensing circuitry. As such, PD 12A may utilize a smaller capacity battery than in scenarios where regular EGM sensing for electrical cardiac events is performed.

For example, ICD 10A may be configured to sense electrical activity of heart 16A, such as atrial depolarizations or P-waves, and determine when PD 12A should deliver one or more pacing signals (e.g., pulses) to the left ventricle of heart 16A. ICD 10A may then transmit control signals to PD 12A to provide timing information associated with the pacing pulses that are to be delivered. The timing information may be determined based on one or more stored A-V or V-V intervals, which may be determined by processing circuitry, e.g., of ICD 10A and/or PD 12A, as described above. Upon receiving the control signals from ICD 10A, PD 12A may deliver the pacing signals or pulses according to the timing information indicated by the received control signals. ICD 10A and PD 12A may operate using transmission schedules and communication schedules to limit the amount of time that PD 12A operates communication circuitry that receives the control signals in a powered-on state.

In some examples, ICD 10A may also provide pacing signals as part of CRT using sensing electrodes 22A and/or 22B of defibrillation lead 18A. In other examples, ICD 10A may be coupled to one or more intracardiac leads carrying respective electrodes configured to be disposed within the right atrium and the right ventricle of heart 16A, and deliver pacing pulses via these intracardiac leads as part of the CRT along with PD 12A. In other examples, additional PDs like PD 12A may be disposed within the right atrium and/or the right ventricle of heart 16A. Any PD(s) placed within the right atrium and/or right ventricle of heart 16A may be similarly controlled by ICM 10A. Alternatively, one or both PDs in the right atrium and/or right ventricle may provide control signals to PD 12A disposed in the left ventricle of heart 16A.

In another example, PD 12A implanted in the left ventricle and/or a PD implanted in the right ventricle or other heart chamber may be configured to deliver other pacing therapy, such as bradycardia pacing therapy, anti-tachycardia pacing (ATP), and/or post-shock pacing, to heart 16A. For example, PD 12A or a PD implanted in or on the right ventricle may deliver A-V synchronous bradycardia pacing therapy, timed relative to the atrial depolarization based on control signals received from ICD 10A in accordance with the techniques described herein.

Again, in some examples, PD 12A may not include EGM sensing circuitry. In other examples, PD 12A may be capable of sensing electrical signals using the electrodes carried on the housing of PD 12A. These electrical signals may be electrical signals generated by cardiac muscle and indicative of depolarizations (e.g. a ventricular depolarization or R-wave, or an atrial depolarization or P-wave) and repolarizations (e.g. a ventricular repolarization or T-wave) of heart 16A at various times during the cardiac cycle. PD 12A may analyze the sensed electrical signals to detect tachyarrhythmia, such as ventricular tachycardia or ventricular fibrillation, bradyarrhythmia, or even shocks. In response to detecting these conditions, PD 12A may, e.g., depending on the type of arrhythmia or shock, begin to deliver bradycardia pacing therapy or post-shock pacing, with or without information from another device. In some examples, PD 12A may only detect arrhythmias in response to failing to detect control signals from ICM 10A for a predetermined period, or over a predetermined number of communication windows.

Figure 2:
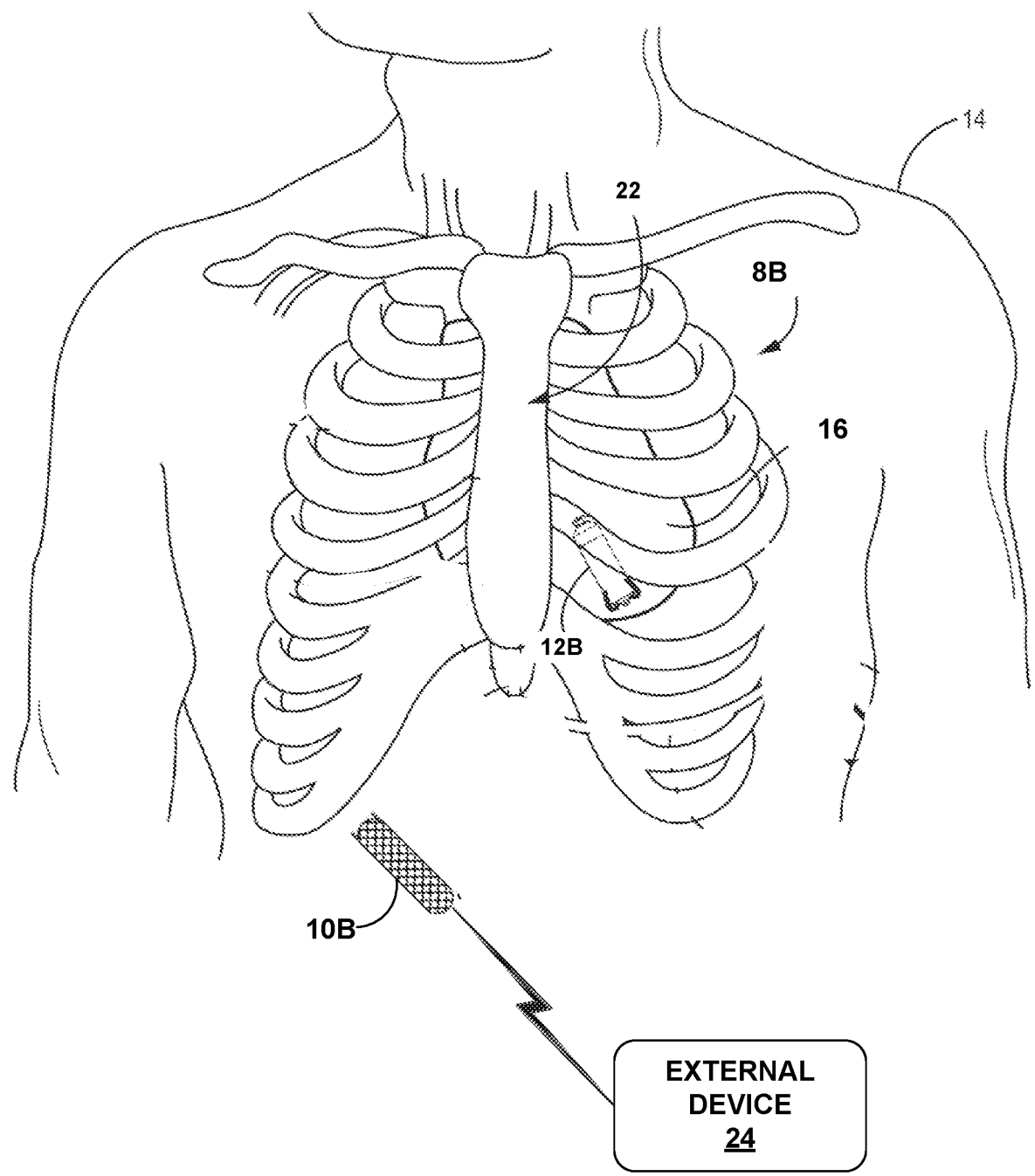
FIG. 2 is a conceptual diagram illustrating an example front view of a patient implanted with another example medical device system that includes an insertable cardiac monitoring (ICM) device that is inserted subcutaneously or substernally in the patient, and a PD implanted within a cardiac chamber of the patient, in accordance with one or more aspects of this disclosure.

Although FIG. 1A is illustrated and described in the context of a substernal ICD system 4A and a PD 12A, techniques in accordance with one or more aspects of the present disclosure may be applicable to other medical device systems. One example of another medical device system 8 that may implement the techniques of this disclosure is shown in FIG. 2 and discussed in further detail below with respect to FIG. 2. In another example, instead of an extravascular ICD (EV-ICD) system, a subcutaneous or submuscular pacing device coupled to a ventricular intracardiac lead may be implanted within the patient. In this manner, the pacing device may provide pacing pulses to the right ventricle of heart 16A via the intracardiac lead, and control PD 12A to provide pacing pulses to the left ventricle of heart 16A. In another example, a subcutaneous or submuscular pacing device coupled to a ventricular intracardiac lead carrying electrodes may be coupled to a motion sensor, e.g. by the lead, another lead, or wirelessly, and may implement the techniques of this disclosure for evaluating contractions during CRT. As such, in some examples, the sensor may be included as a part of an endocardial lead, such as a left-endocardial lead. The examples of FIGS. 1A-1C and 2 are for illustrative purposes and should not be considered limiting of the techniques described herein, in any way.

External device 24 may be configured to communicate with ICD 10A and/or PD 12A. In examples where external device 24 only communicates with one of ICD 10A or PD 12A, the non-communicative device may receive instructions from or transmit data to the device in communication with external device 24. In some examples, external device 24 may include, be, or be part of one or more of a handheld computing device, a computer workstation, or a networked computing device. External device 24 may include a user interface that is configured or otherwise operable to receive input from a user. In other examples, external device 24 may process user interactions that are relayed remotely, such as via a networked computing device. External device 24 may process user interactions to enable users to communicate with PD 12A and/or ICD 10A. For example, external device 24 may process user inputs to send an interrogation request and retrieve therapy delivery data, to update therapy parameters that define therapy, to manage communication between PD 12A and/or ICD 10A, or to perform any other activities with respect to PD 12A and/or ICD 10A. Although the user is typically a physician, technician, surgeon, electrophysiologist, or other healthcare professional, the user may be patient 14 in some examples.

External device 24 may also allow the user to define how PD 12A and/or ICD 10A senses electrical signals (e.g., cardiac electrograms (EGMs)), detects arrhythmias (e.g., tachyarrhythmias), delivers therapy (e.g., CRT), and communicates with other devices of cardiac medical device system 8A. For example, external device 24 may be used to change tachyarrhythmia detection parameters. In another example, external device 24 may be used to manage therapy parameters. When PD 12A and ICD 10A are configured to communicate with each other, external device 24 may be used to alter communication protocols between PD 12A and ICD 10A. For example, external device 24 may instruct PD 12A and/or ICD 10A to switch between one-way and two-way communication and/or change which of PD 12A and/or ICD 10A are tasked with initial detection of arrhythmias.

External device 24 may also allow a user to program A-V and/or V-V intervals for CRT. For example, external device 24A may allow a user to select an A-V interval, and program ICD 10A to trigger PD 12A to deliver ventricular pacing pulse at certain time after a detected P-wave based on the selected A-V interval, or program PD 12A to deliver ventricular pacing pulse at a certain time after a trigger signal from ICD 10A based on the selected A-V interval. External device 24 may also, or alternatively, be configured to adjust parameters defining communication such as the duration of windows, the rate of windows, rate of synchronization signals, allowable lapses in communication before one or more devices attempt to re-establish communication, and other such parameters. External device 24 may also allow a user to program parameters used by processing circuitry, e.g., of ICD 10A, PD 12A, and/or external device 24, to identify features of a cardiac contraction within a motion signal, and determine whether the cardiac contraction is a fusion beat or another type of beat, such as an intrinsic beat or fully-paced beat, based on the one or more features, according to the techniques of this disclosure.

External device 24 may communicate with PD 12A and/or ICD system 4A via wireless communication using any techniques known in the art. Examples of communication techniques may include, for example, proprietary and non-proprietary radiofrequency (RF) telemetry, inductive telemetry, acoustics, and tissue conduction communication (TCC), but other techniques are also contemplated. During TCC, current is driven through the tissue between two or more electrodes of a transmitting device. The electrical signal spreads and can be detected at a distance by measuring the voltage generated between two electrodes of a receiving device.

In some examples, PD 12A and ICD 10A may engage in communication to facilitate the appropriate detection of arrhythmias and/or appropriate delivery of pacing therapy. The communication may include one-way communication in which one device is configured to transmit communication messages and the other device is configured to receive those messages according to the respective schedule. The communication may instead include two-way communication in which each device is configured to transmit and receive communication messages. Both of PD 12A and ICD 10A may be configured to toggle between one-way communication modes and two-way communication modes based on the therapy that patient 14 may need. The communication may be via TCC or other communication signals, e.g., RF communication signals.

Although PD 12A may at least partially determine if PD 12A delivers CRT or another therapy to patient 14, PD 12A in some examples may perform one or more functions in response to receiving a request from ICD 10A and without any further analysis by PD 12A. In this manner, ICD 10A may act as a master device and PD 12A may act as a slave device.

Although ICD 10A and PD 12A may perform coordinated communication to provide CRT and other pacing therapies, these medical devices may provide other therapies to patient 14 using transmission and communication schedules described herein. For example, ICD 10A may be a subcutaneous, substernal, or transvenous device (although discussed as a substernal device with respect to FIG. 1A) that detects the atrial depolarization (i.e., P-wave) and transmits the control signal telling a leadless pacer in the left ventricle (LV) (e.g., PD 12A) when to deliver a pacing signal to add CRT to the functionality of ICD 10A. In another example, any device may be implanted subcutaneously in the torso of patient 14 to detect the atrial depolarization (P-wave) and transmit a control signal to PD 12A in the left ventricle, or PDs in both ventricles, to deliver CRT or other forms of ventricular pacing to heart 16A timed to the occurrence of the atrial depolarization.

In another example, two PDs (e.g., including PD 12A illustrated in FIG. 1A) may be in communication during ventricular pacing with atrial sensing (VDD) with one PD in the right ventricle to detect the P-wave, deliver pacing signals to and sense activity from the right ventricle, and send a TCC or other signal to PD 12A in the left ventricle to deliver a pacing signal to implement atrial synchronous bi-ventricular (bi-V) pacing. This pacing mode may avoid pacing on a T-wave following a PVC because the PD implanted in the right ventricle may provide sensing and provides backup ventricular pacing and sensing with ventricular event inhibition (VVI) pacing therapy if the TCC signals between the devices are lost.

FIG. 2 is a conceptual diagram illustrating an example front view of patient 14 implanted with another example medical device system 8B that includes an insertable cardiac monitoring (ICM) device 10B that is inserted subcutaneously or substernally in the patient, and PD 12B implanted either epicardially or within a cardiac chamber of patient 14, in accordance with one or more aspects of this disclosure. Components illustrated in FIG. 2 with like numbers of those of FIGS. 1A-1C may be similarly configured and may provide similar functionality to the similarly-numbered components illustrated in FIGS. 1A-1C. Medical device system 8B of FIG. 2 may leverage cardiac signal sensing capabilities of ICM 10B or PD 12B to perform one or more of the techniques described herein with respect to optimizing the operation of PD 12B and the collecting, measuring, and storing various forms of diagnostic data, including generating any corresponding reports or alerts. In certain cases, ICM 10B or PD 12B may directly analyze collected diagnostic data and generate any corresponding reports or alerts. In some cases, however, ICM 10B or PD 12B may send diagnostic data to external device 24. In some examples, ICM 10B may take the form of a Reveal LINQ™ ICM, available from Medtronic plc, of Dublin, Ireland.

Medical device system 8A of FIGS. 1A-1C and medical device system 8B of FIG. 2 may each be configured to perform the CRT adaptation and the tabulating and reporting of CRT diagnostic data techniques of this disclosure. As such, the CRT adaptation and reporting techniques of this disclosure are described hereinafter as being performed generically by "medical device system 8," "implantable medical device (IMD) 10," which may include as examples ICD 10A and ICM 10B, and/or "PD 12," although it will be appreciated that the described techniques may be performed by the respective corresponding systems/devices illustrated in FIGS. 1A-1C or FIG. 2. In accordance with various aspects of this disclosure, medical device system 8 and/or components thereof may be configured to detect activity of heart 16, and deliver pacing therapy in a timed relationship to such activity based on a stored interval, e.g., an A-V or V-V interval. As examples, medical device system 8 may store interval information adapted according to the techniques described in this disclosure, or other programming or diagnostic data, to one or more memory devices that are included in the components illustrated in FIGS. 1A-1C and 2, and/or to memory device(s) that are otherwise communicatively coupled to one or more of the illustrated components of medical device system 8.

As described above, IMDs 10 may, in various examples, represent different types of cardiac monitoring (and in some cases therapy) devices that can be implanted substernally, subcutaneously, or elsewhere in the body of patient 14. In any of these implementations, IMD 10 includes interface hardware and sensing circuitry that senses a cardiac signal that varies as a function of a cardiac cycle of heart 16. For instance, the sensing circuitry of IMD 10 may detect the timing of cardiac depolarization and/or mechanical cardiac contraction events, based on the cardiac signal that varies as a function of the cardiac cycle.

Based on signals from such sensing circuitry, or based on other information (e.g., indicating delivery of pacing pulse), processing circuitry of IMD 10 may detect the occurrence of atrial and/or ventricular depolarizations (paced or intrinsic), or other atrial or ventricular events or fiducials from which to set the beginning or end of an A-V or V-V timing interval. In response to detection of the depolarizations, the processing circuitry may trigger PD 12 to deliver ventricular pacing pulses for CRT. The delivery of ventricular pacing pulses for CRT may be timed based on a stored A-V or V-V interval and the time that the detected atrial or ventricular depolarization occurred.

According to the techniques of this disclosure, a motion sensor within or coupled to PD 12, e.g., a three-axis accelerometer, may generate a signal that indicates mechanical activity of the heart, including contractions, during the delivery of CRT. According to the techniques of this disclosure, processing circuitry, e.g., of PD 12, IMD 10, external device 24, and/or any device described herein, may identify one or more features of cardiac contractions with the motion signal, and determine whether the cardiac contraction is one of a fusion beat, intrinsic beat, or fully-paced beat based on the one or more features. Fusion beats are desired, and the processing circuitry may adapt the CRT pacing control parameter values, e.g., the A-V, V-V or other timing intervals, to achieve fusion beats based on detection of one or more of the other types of beats. The processing circuitry may also generate diagnostic information based on the numbers of beats of the different types (e.g., fusion vs. non-fusion), which may be reported to a user. The diagnostic information may include values of one or more metrics indicating an amount, e.g., a percentage, of beats that are fusion beats or otherwise effectively captured the heart.

Figure 3:
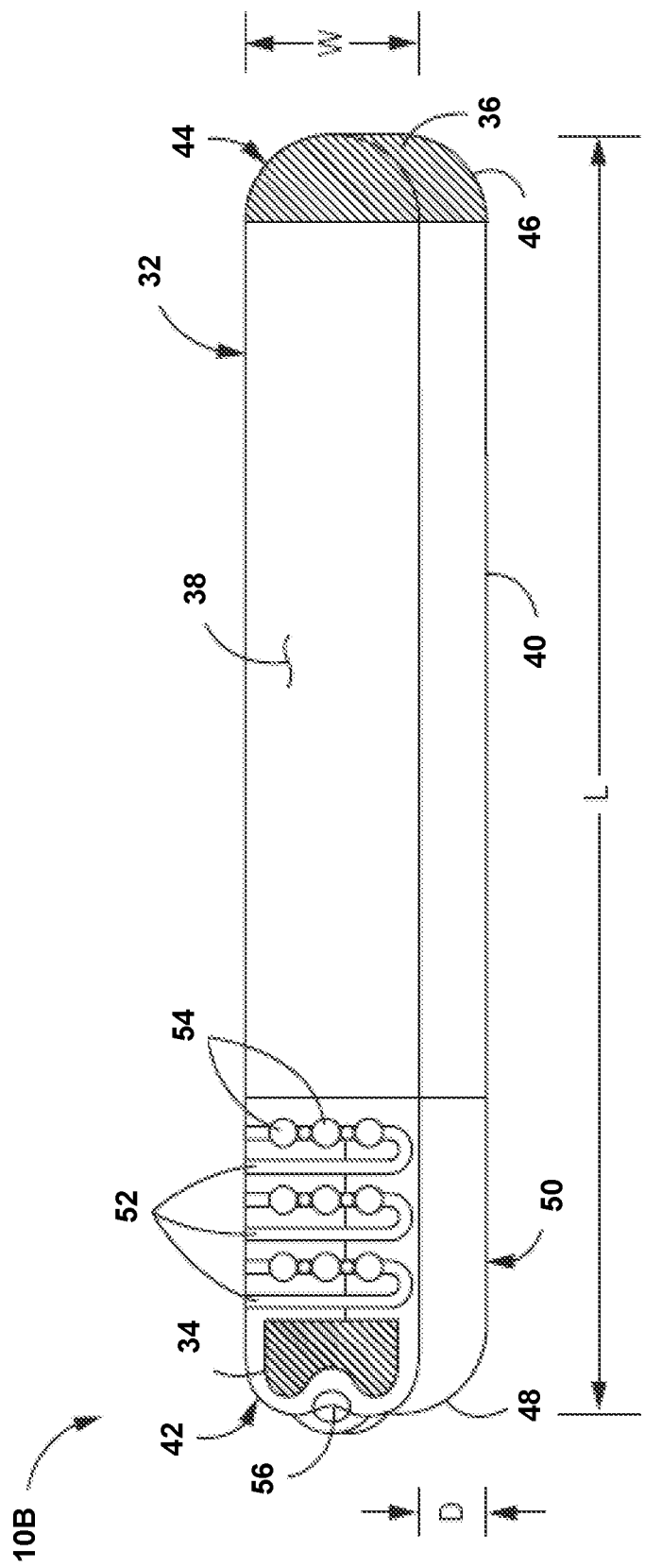
FIG. 3 is a conceptual drawing illustrating an example configuration of the ICM device illustrated in FIG. 2, in accordance with one or more aspects of this disclosure.

FIG. 3 is a conceptual drawing illustrating an example configuration of ICM 10B illustrated in FIG. 2. In the example shown in FIG. 3, ICM 10B may be embodied as a monitoring device having housing 32, proximal electrode 34 and distal electrode 36. Housing 32 may further include first major surface 38, second major surface 40, proximal end 42, and distal end 44. Housing 32 encloses electronic circuitry located inside the ICM 10B and protects the circuitry contained therein from body fluids. Electrical feedthroughs provide electrical connection of electrodes 34 and 36.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 34 and distal electrode 36 may range from thirty millimeters (mm) to fifty-five mm, thirty-five mm to fifty-five mm, and from forty mm to fifty-five mm and may be any range or individual spacing from twenty-five mm to sixty mm.

In addition, ICM 10B may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 38 may range from three mm to ten mm and may be any single or range of widths between three mm and ten mm. The thickness of depth D of ICM 10B may range from two mm to nine mm. In other examples, the depth D of ICM 10B may range from two mm to five mm and may be any single or range of depths from two mm to nine mm.

Furthermore, ICM 10B according to an example of the present disclosure is has a geometry and size designed for ease of implant and patient comfort. Examples of ICM 10B described in this disclosure may have a volume of three cubic centimeters (cm) or less, one-and-a-half cubic cm or less or any volume between three and one-and-a-half cubic centimeters. In addition, in the example shown in FIG. 3, proximal end 42 and distal end 44 are rounded to reduce discomfort and irritation to surrounding tissue once inserted under the skin of the patient. In some examples, ICM 10B, including instrument and method for inserting ICM 10B is configured as described, for example, in U.S. Patent Publication No. 2014/0276928, which is entitled, "SUBCUTANEOUS DELIVERY TOOL," and published on Sep. 18, 2014. U.S. Patent Publication No. 2014/0276928 to Vanderpool et al. is incorporated herein by reference in its entirety. In some examples, ICM 10B is configured as described, for example, in U.S. Patent Publication No. 2016/0310031, which is entitled, "METHOD AND APPARATUS FOR DETERMINING A PREMATURE VENTRICULAR CONTRACTION IN A MEDICAL MONITORING DEVICE," and published on Oct. 27, 2016. U.S. Patent Publication No. 2016/0310031 to Sarkar is incorporated herein by reference in its entirety.

In the example shown in FIG. 3, once inserted within the patient, the first major surface 38 faces outward, toward the skin of the patient while the second major surface 40 is located opposite the first major surface 38. Consequently, the first and second major surfaces may face in directions along a sagittal axis of patient 14A (e.g., see FIG. 2), and this orientation may be consistently achieved upon implantation due to the dimensions of ICM 10B. Additionally, an accelerometer, or axis of an accelerometer, may be oriented along the sagittal axis.

Proximal electrode 34 and distal electrode 36 are used to sense cardiac signals, e.g., cardiac EGM signals, intra-thoracically or extra-thoracically, which may be sub-muscularly or subcutaneously. EGM signals may be stored in a memory of the ICM 10B, and EGM data may be transmitted via integrated antenna 52 to another medical device, which may be another implantable device or an external device, such as external device 14A. In some example, electrodes 34 and 36 may additionally or alternatively be used for sensing any bio-potential signal of interest, which may be, for example, any EGM, electroencephalogram (EEG), electromyogram (EMG), or a nerve signal, from any implanted location.

In the example shown in FIG. 3, proximal electrode 34 is close to the proximal end 42, and distal electrode 36 is close to distal end 44. In this example, distal electrode 36 is not limited to a flattened, outward facing surface. Distal electrode 36 may extend from first major surface 38 around rounded edges 46 and/or end surface 48 and onto the second major surface 40 so that the electrode 36 has a three-dimensional curved configuration. In the example shown in FIG. 3, proximal electrode 34 is located on first major surface 38 and is substantially flat, outward facing. However, in other examples, proximal electrode 34 may utilize the three-dimensional curved configuration illustrated with respect to distal electrode 36 in FIG. 3, providing a three-dimensional proximal electrode. In other examples still, distal electrode 36 may utilize a substantially flat, outward facing electrode located on first major surface 38 like that shown in FIG. 3 with respect to proximal electrode 34.

The various electrode configurations allow for configurations in which proximal electrode 34 and distal electrode 36 are located on both first major surface 38 and second major surface 40. In other configurations, such as the configuration shown in FIG. 3, only one of proximal electrode 34 or distal electrode 36 is located on both major surfaces 38 and 40. In still other configurations, both proximal electrode 34 and distal electrode 36 are located on one of the first major surface 38 or the second major surface 40 (i.e., proximal electrode 34 may be located on first major surface 38 while distal electrode 36 may be located on second major surface 40). In another example, ICM 10B may include electrodes on both major surface 38 and 40 at or near the proximal and distal ends of the device, such that a total of four electrodes are included on ICM 10B. Electrodes 34 and 36 may be formed of a plurality of different types of biocompatible conductive material, e.g., stainless steel, titanium, platinum, iridium, or alloys thereof, and may utilize one or more coatings such as titanium nitride or fractal titanium nitride.

In the example shown in FIG. 3, proximal end 42 includes a header assembly 50 that includes one or more of proximal electrode 34, integrated antenna 52, anti-migration projections 54, and/or suture hole 56. Integrated antenna 52 is located on the same major surface (i.e., first major surface 38) as proximal electrode 34 and is also included as part of header assembly 50. Integrated antenna 52 allows ICM 10B to transmit and/or receive data. In other examples, integrated antenna 52 may be formed on the opposite major surface as proximal electrode 34, or may be incorporated within the housing 32 of ICM 10B. In the example shown in FIG. 3, anti-migration projections 54 are located adjacent to integrated antenna 52 and protrude away from first major surface 38 to prevent longitudinal movement of the device. In the example shown in FIG. 3 anti-migration projections 54 includes a plurality (e.g., nine) small bumps or protrusions extending away from first major surface 38.

As discussed above, in other examples, anti-migration projections 54 may be located on the opposite major surface as proximal electrode 34 and/or integrated antenna 52. In addition, in the example shown in FIG. 3 header assembly 50 includes suture hole 56, which provides another means of securing ICM 10B to the patient to prevent movement following insert. In the example shown, suture hole 56 is located adjacent to proximal electrode 34. In one example, header assembly 50 is a molded header assembly made from a polymeric or plastic material, which may be integrated or separable from the main portion of ICM 10B.

Figure 4:
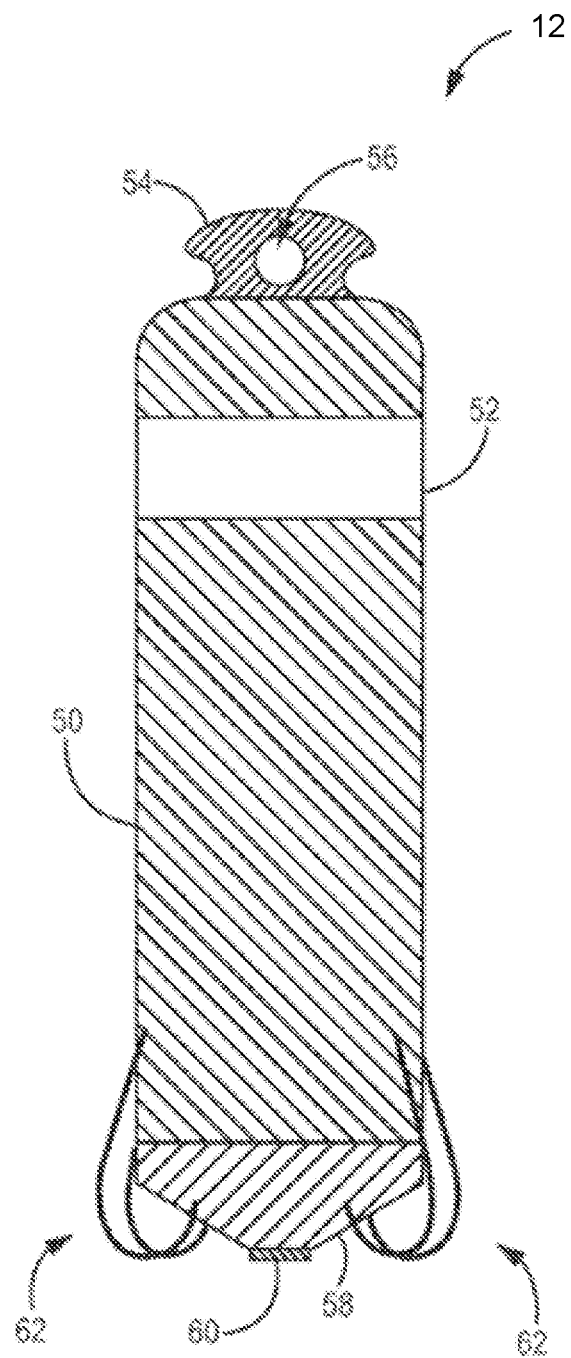
FIG. 4 is a conceptual drawing illustrating an example configuration of a PD in accordance with one or more aspects of this disclosure.

FIG. 4 is a conceptual drawing illustrating an example PD 12, which may correspond to either or both of PD 12A of FIG. 1A or PD 12B of FIG. 2. As shown in FIG. 4, PD 12 includes case 50, cap 58, electrode 60, electrode 52, fixation mechanisms 62, flange 54, and opening 56. Together, case 50 and cap 58 may be considered the housing of PD 12. In this manner, case 50 and cap 58 may enclose and protect the various electrical components within PD 12. Case 50 may enclose substantially all the electrical components, and cap 58 may seal case 50 and create the hermetically sealed housing of PD 12. Although PD 12 is generally described as including one or more electrodes, PD 12 may typically include at least two electrodes (e.g., electrodes 52 and 60) to deliver an electrical signal (e.g., therapy such as CRT) and/or provide at least one sensing vector. Electrodes 52 and 60 are carried on the housing created by case 50 and cap 58. In this manner, electrodes 52 and 60 may be considered leadless electrodes.

In the example of FIG. 4, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode, and electrode 52 may be used as an anode, or vice versa, for delivering CRT or other appropriate cardiac therapy (bradycardia pacing, ATP, post-shock pacing, etc.). However, electrodes 52 and 60 may be used in any stimulation configuration. In addition, electrodes 52 and 60 may be used to detect intrinsic electrical signals from cardiac muscle. In other examples, PD 12 may include three or more electrodes, where each electrode may deliver therapy and/or detect intrinsic signals. CRT and other pacing delivered by PD 12 may be "painless" to patient 14 or even undetectable by patient 14 since the electrical stimulation occurs very close to or at cardiac muscle and at relatively low energy levels compared with alternative devices.

Fixation mechanisms 62 may attach PD 12 to cardiac tissue. Fixation mechanisms 62 may be active fixation tines, screws, clamps, adhesive members, or any other types of attaching a device to tissue. As shown in the example of FIG. 4, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of PD 12. For example, a suture or other device may be inserted around flange 54 and/or through opening 56 and attached to tissue. In this manner, flange 54 may provide a secondary attachment structure to tether or retain PD 12 within heart 16 if fixation mechanisms 62 fail. Flange 54 and/or opening 56 may also be used to extract PD 12 once the PD needs to be explanted (or removed) from patient 14 if such action is deemed necessary.

In another example, PD 12 may be configured to be implanted external to heart 16, e.g., near or attached to the epicardium of heart 16. An electrode carried by the housing of the fusion pacing PD 12 may be placed in contact with the epicardium and/or one or more electrodes placed in contact with the epicardium at locations sufficient to provide therapy (e.g., on external surfaces of the left and/or right ventricles). In any example, IMD 10 may communicate with one or more leadless or leaded devices implanted internal or external to heart 16.

Figure 5:
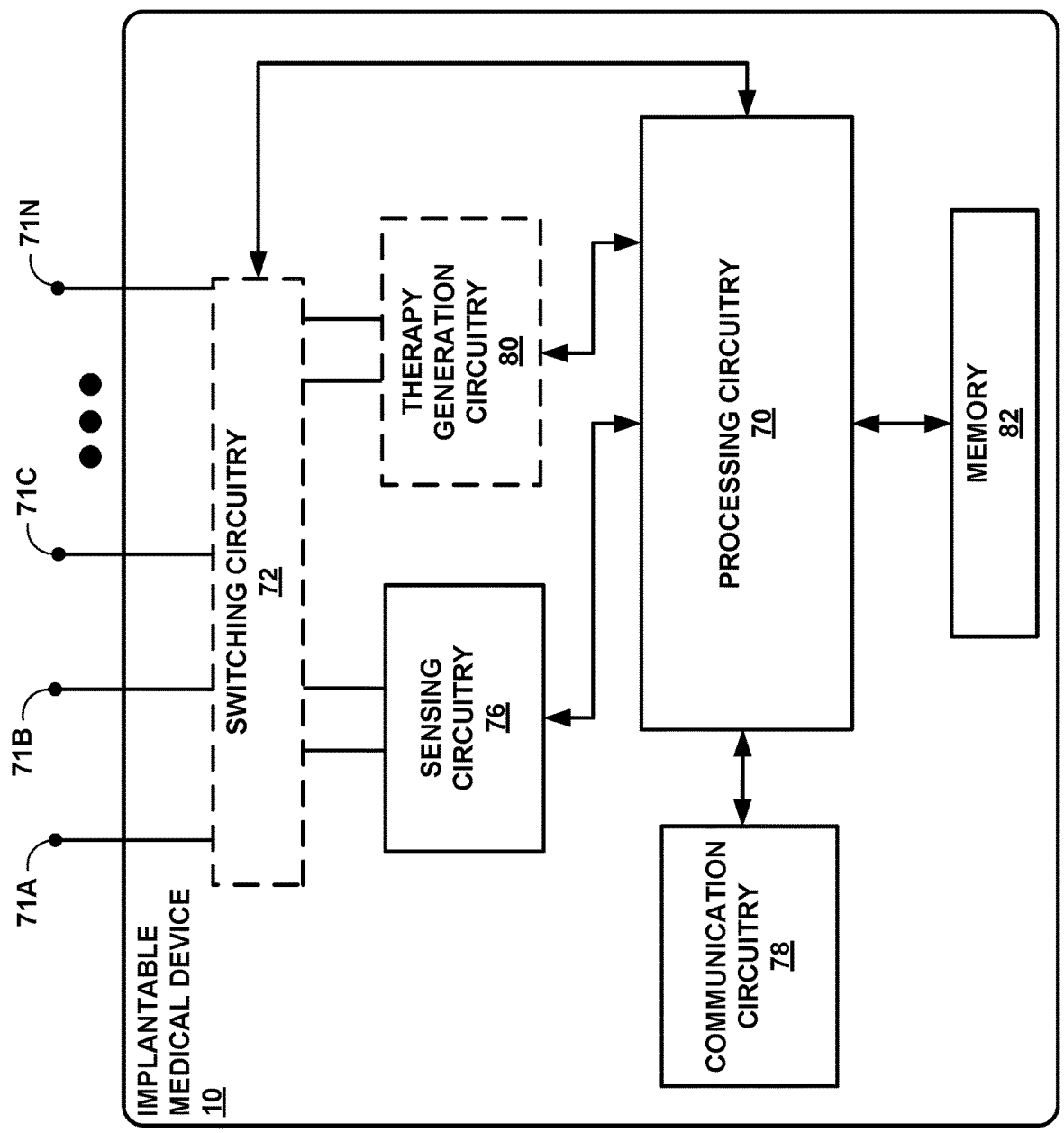
FIG. 5 is a functional block diagram illustrating an example configuration of an IMD in accordance with one or more aspects of this disclosure.

FIG. 5 is a block diagram of an example configuration of an IMD 10 that is configured according to one or more aspects of this disclosure. IMD 10 of FIG. 5 may, in various use case scenarios, represent an example of ICD 10A of FIGS. 1A-1C or ICM 10B of FIG. 2. IMD 10 includes two or more electrodes 71A-N (collectively "electrodes 71"), which may correspond to defibrillation electrodes 20 (FIGS. 1A-C), sensing electrodes 22 FIGS. 1A-C), one or more housing electrodes of ICD 10A (FIGS. 1A-C), or electrodes 34 and 36 (FIG. 3).

IMD 10 may include processing circuitry 70 for controlling sensing circuitry 76, communication circuitry 78, (optionally) switching circuitry 72, memory 82, and (optionally) therapy generation circuitry 80. The optional nature of switching circuitry 72 and therapy generation circuitry 80 is shown using dashed-line borders to indicate the optional aspect, in FIG. 5. As one example, therapy generation circuitry 80 is indicated as optional because some embodiments of an IMD configured as an ICM do not deliver therapy. Switching circuitry 72 may include one or more switches, such as metal-oxide-semiconductor field-effect transistors (MOSFETs) or bipolar transistors. Processing circuitry 70 may control switching circuitry 72 to connect selected groupings of electrodes 71 to sensing circuitry 76 to sense one or more physiological electrical signals.

Sensing circuitry 76 is configured to receive cardiac electrical signals from selected combinations of two or more electrodes 71, and sense cardiac events attendant to depolarization and repolarization of cardiac tissue. Sensing circuitry 76 may include one or more sensing channels, each of which may be selectively coupled to respective combinations of electrodes 71 to detect electrical activity of a particular chamber of heart 16, e.g., one or more atrial and/or ventricular sensing channels. Each sensing channel may be configured to amplify, filter and rectify the cardiac electrical signal received from selected electrodes coupled to the respective sensing channel to detect cardiac events, e.g., P-wave and R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 76 may output an indication to processing circuitry 70 in response to sensing a cardiac event in a chamber of interest, e.g., a P-wave or R-wave. In this manner, processing circuitry 70 may receive detected cardiac event signals corresponding to the occurrence of detected P-waves and R-waves. Indications of detected R-waves may be used by processing circuitry 70 for detecting ventricular arrhythmia episodes, and indications of detected P-waves may be used by processing circuitry 70 for detecting atrial arrhythmia episodes. Sensing circuitry 76 may also pass one or more digitized EGM signals to processing circuitry 70 for analysis, e.g., for use in cardiac rhythm discrimination and for morphological analysis.

Communication circuitry 78 may include circuitry for generating and modulating, and in some cases receiving and demodulating, continuous and/or pulsatile communication waveforms. Communication circuitry 78 may be configured to transmit and/or receive one or both of RF signals via an antenna (not shown) or TCC signals via electrodes 71. Although not shown in FIG. 5, communication circuitry 78 may be coupled to a selected two or more electrodes 71 via switching circuitry 72 for TCC.

In some examples, processing circuitry 70 may control switching circuitry 72 to connect electrodes 71 to therapy generation circuitry 80 to deliver a therapy pulse, such as a pacing, cardioversion, or defibrillation pulse to the heart. Therapy generation circuitry 80 is electrically coupleable to electrodes 71, and is configured to generate and deliver electrical therapy to heart 16 via selected combinations of electrodes 71. Therapy generation circuitry 80 may include charging circuitry, and one or more charge storage devices, such as one or more high voltage capacitors and/or one or more low voltage capacitors. Switching circuitry 72 may control when the capacitor(s) are discharged to selected combinations of electrodes 71. Therapy generation circuitry 80 and/or processing circuitry 70 may control the frequency, amplitude, and other characteristics of the therapy pulses. Therapy generation circuitry 80 may deliver the therapy pulses to electrodes 71 when switching circuitry 72 connects therapy generation circuitry 80 to electrodes 71.

Processing circuitry 70 may control switching circuitry 72 by sending control signals to the control terminals of one or more switches of switching circuitry 72. The control signals may control whether the switches of switching circuitry 72 conduct electricity between the load terminals of the switches. If switching circuitry 72 includes MOSFET switches, the control terminals may include gate terminals, and the load terminals may include drain terminals and source terminals.

Processing circuitry 70 may include various types of hardware, including one or more microprocessors, DSPs, ASICs, FPGAs, or any other equivalent integrated or discrete logic circuitry, as well as any combinations of such components. The term "processing circuitry" may generally refer to any of the foregoing logic circuitry, alone or in combination with other logic circuitry, or any other equivalent circuitry. Processing circuitry 70 represents hardware that can be configured to implement firmware and/or software that sets forth one or more of the algorithms described herein. Memory 82 includes computer-readable instructions that, when executed by processing circuitry 70, cause IMD 10 and processing circuitry 70 to perform various functions attributed to IMD 10 and processing circuitry 70 herein. Memory 82 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

In some examples, processing circuitry 70 receives indications of the occurrence of P-waves or other atrial events (or R-wave or other ventricular events) from sensing circuitry 76, or identifies the occurrence of P-waves or other atrial events by processing of a far-field EGM signal received from sensing circuitry using any of a variety of techniques known in the art. In response to the atrial or ventricular event, processing circuitry 70 may control communication circuitry 78 to transmit a signal to intracardiac PD 12. The signal causes intracardiac PD 12 to deliver a ventricular pacing pulse for CRT, absent an intrinsic ventricular depolarization prior to expiration of a timing interval, such as an A-V or V-V interval. As described above, one or both of IMD 10 and intracardiac PD 12 may store adjustable timing intervals that control the delivery of CRT based on an A-V interval or V-V interval. IMD 10 may store such intervals in memory 82.

In some examples, processing circuitry 70 of IMD 10 may receive a motion signal from a sensor of intracardiac PD 12 that indicates mechanical activity of the heart, e.g., motion of the intracardiac PD and its sensor within the heart during contraction. Processing circuitry 70 may, according to the techniques described herein, identify one or more features of a cardiac contraction within the signal, determine whether the cardiac contraction is a fusion beat based on the one or more features, and control a timing interval or other control parameter value for delivery of ventricular pacing for CRT by PD 12 based on the determination. Processing circuitry 70 may control a timing interval stored in memory 82 and, for example, used by the processing circuitry to determine when to transmit a signal to PD 12 or when to instruct PD to deliver a ventricular pacing pulse. Processing circuitry 70 may transmit a signal to intracardiac PD 12 via communication circuitry 78 to adjust a timing interval used by the intracardiac PD. Processing circuitry 70 may also determine values of one more metrics that indicate the effectiveness of CRT based on the determination of whether the contractions during CRT are fusion beats according to the techniques described herein.

Existing techniques for illustrating the effectiveness of CRT include determining the percentage of beats that are paced. Such techniques however, do not account for whether the paced beats successfully captured the heart. IMDs implementing the EffectivCRT™ algorithm, available from Medtronic plc of Dublin, Ireland, determine the percentage or other amount of CRT pacing that was actually effective in capturing the heart, e.g., based on the morphology of resulting cardiac signal in a particular observation vector, such as from a left-ventricular pacing cathode to a right-ventricular coil electrode in a system including such electrodes. An example of EffectivCRT™ is described in U.S. Pat. No. 8,750,998 to Ghosh et al., which is entitled, "EFFECTIVE CAPTURE TEST," and issued on Jun. 10, 2014. U.S. Pat. No. 8,750,998 to Ghosh et al. is incorporated herein by reference in its entirety. Another example of use of the EffectivCRT™ algorithm to maintain effective CRT during atrial fibrillation is described in U.S. Patent Publication No. 2014/0277245 to Lu et al., which is entitled, "MODULATE PACING RATE TO INCREASE THE PERCENTAGE OF EFFECTIVE VENTRICULAR CAPTURE DURING ATRIAL FIBRILLATION," and published on Sep. 18, 2014. U.S. Patent Publication No. 2014/0277245 to Lu et al. is incorporated herein by reference in its entirety.

Figure 6:
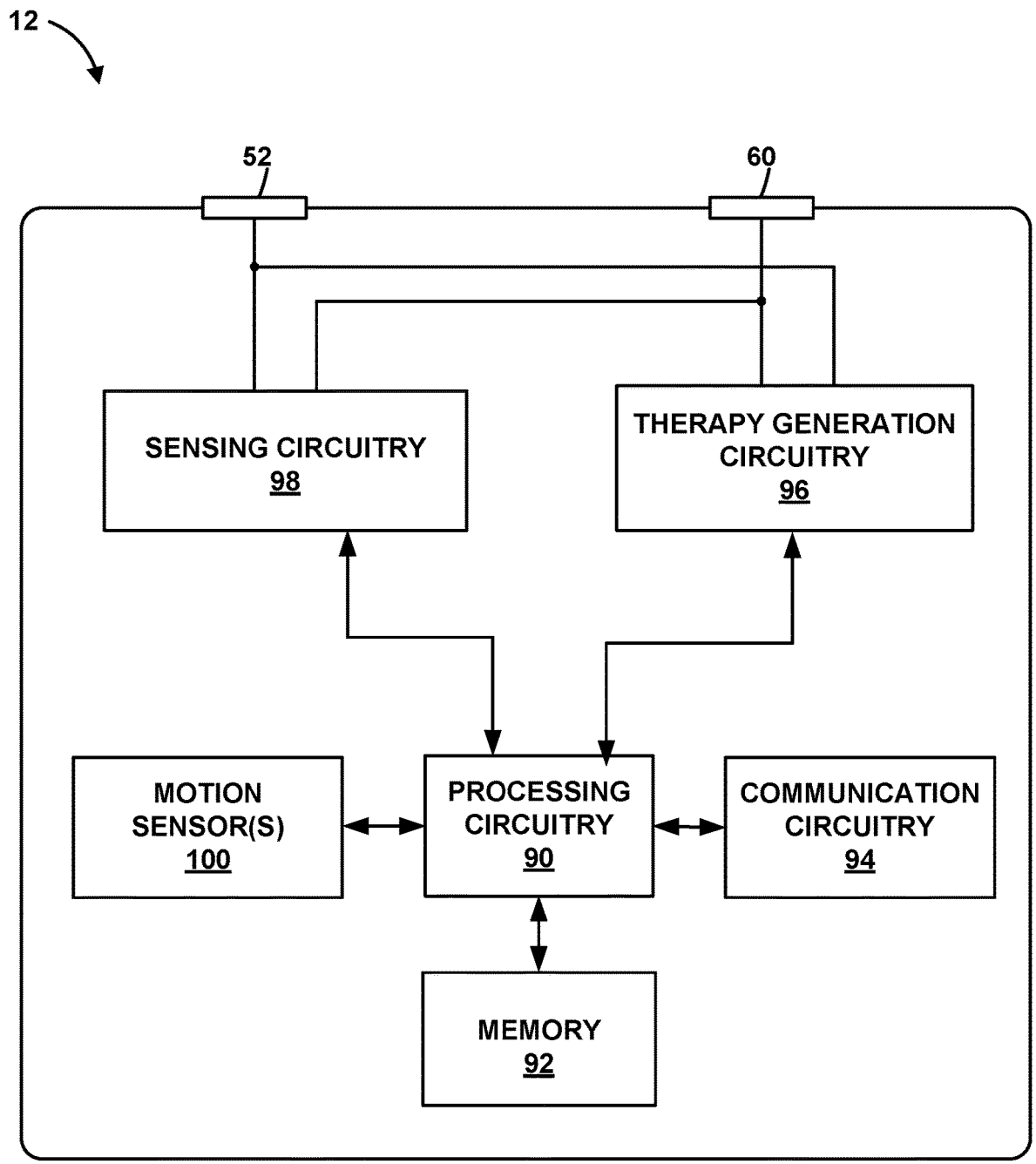
FIG. 6 is a functional block diagram illustrating an example configuration of a PD in accordance with one or more aspects of this disclosure.

FIG. 6 is a functional block diagram illustrating an example configuration of PD 12, which may correspond to PD 12A of FIGS. 1A-1C or PD 12B of FIG. 2. In the illustrated example, PD 12 includes processing circuitry 90, memory 92, therapy generation circuitry 96, sensing circuitry 98, motion sensor 100, and communication circuitry 94. Memory 92 includes computer-readable instructions that, when executed by processing circuitry 90, cause PD 12 and processing circuitry 90 to perform various functions attributed to PD 12 and processing circuitry 90 herein (e.g., analyzing a motion signal from sensor 100 that indicates mechanical activity of the heart, e.g., motion of the intracardiac PD and sensor 100 within the heart during contraction, identifying one or more features of a cardiac contraction within the signal, determining whether the cardiac contraction is a fusion beat based on the one or more features, controlling a timing interval for delivery of ventricular pacing for CRT by therapy generation circuitry 96 based on the determination, and determining values of one more metrics that indicate the effectiveness of CRT based on the determination). Memory 92 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media.

Processing circuitry 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processing circuitry 90 herein may be embodied as software, firmware, hardware or any combination thereof.

Processing circuitry 90 controls therapy generation circuitry 96 to deliver stimulation therapy to heart 16 according to therapy parameters, which may be stored in memory 92. For example, processing circuitry 90 may control therapy generation circuitry 96 to deliver electrical pulses with the amplitudes, pulse widths, frequency, or electrode polarities specified by the therapy parameters. In this manner, therapy generation circuitry 96 may deliver pacing pulses (e.g., fusion pacing for CRT) to heart 16 via electrodes 52 and 60. Although PD 12 may only include two electrodes, e.g., electrodes 52 and 60, PD 12 may utilize three or more electrodes in other examples. PD 12 may use any combination of electrodes to deliver therapy and/or detect electrical signals from patient 14.

Therapy generation circuitry 96 is electrically coupled to electrodes 52 and 60 carried on the housing of PD 12. In the illustrated example, therapy generation circuitry 96 is configured to generate and deliver electrical stimulation therapy to heart 16. For example, therapy generation circuitry 96 may deliver pulses to a portion of cardiac muscle within heart 16 via electrodes 52 and 60. In some examples, therapy generation circuitry 96 may deliver pacing stimulation in the form of electrical pulses. In other examples, signal generator may deliver one or more of these types of stimulation in the form of other signals, such as sine waves, square waves, or other substantially continuous time signals. Therapy generation circuitry 96 may include charging circuitry, and one or more charge storage devices, such as one or more capacitors. Switching circuitry (not shown) may control when the capacitor(s) are discharged to electrodes 52 and 60.

Sensing circuitry 98 monitors signals from at least one of electrodes 52 and 60 to monitor electrical activity of heart 16, impedance, or another electrical phenomenon. Sensing may be done to determine heart rates or heart rate variability, or to detect ventricular dyssynchrony, arrhythmias (e.g., tachyarrhythmias) or other electrical signals. Sensing circuitry 98 may include switching circuitry to select the electrode polarity used to sense the heart activity. In examples with more than two electrodes, processing circuitry 90 may select the electrodes that function as sense electrodes, i.e., select the sensing configuration, via the switching circuitry within sensing circuitry 98. Sensing circuitry 98 may include one or more detection channels, each of which may be coupled to a selected electrode configuration for detection of cardiac signals via that electrode configuration. Some detection channels may be configured to detect cardiac events, such as R-waves, and provide indications of the occurrences of such events to processing circuitry 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 90 may control the functionality of sensing circuitry 98 by providing signals via a data/address bus.

In addition to detecting and identifying specific types of cardiac rhythms (types of cardiac events), sensing circuitry 98 may also sample the detected intrinsic signals to generate an electrogram or other time-based indication of cardiac events. Processing circuitry 90 may also be able to coordinate the delivery of pacing pulses from different PDs, e.g., implanted in different chambers of heart 16, such as an PD implanted in the other ventricle. For example, processing circuitry 90 may identify delivered pulses from other PDs via sensing circuitry 98 and updating pulse timing. In other examples, PDs may communicate with each other via communication circuitry 94 and/or instructions over a carrier wave (such as a stimulation waveform).

Memory 92 may be configured to store a variety of operational parameters, therapy parameters, sensed and detected data, and any other information related to the therapy and treatment of patient 14. In the example of FIG. 6, memory 92 may store sensed EGMs, signals received from motion sensor 100, communications from IMD 10, therapy parameter values, such as timing intervals that control the timing of CRT pacing pulses or other CRT control parameter values, information indicating whether cardiac contractions during CRT were fusion or other beats, and values of one or more metrics that indicate CRT effectiveness. In some examples, memory 92 may act as a temporary buffer for storing data until it can be uploaded to IMD 10, another implanted device, or external device 24.

Motion sensor 100 may be contained within the housing of PD 12 and include one or more accelerometers, gyroscopes, electrical or magnetic field sensors, or other devices capable of detecting motion and/or position of PD 12. For example, motion sensor 100 may include a 3-axis accelerometer (three-dimensional accelerometer) that is configured to detect accelerations in any direction in space. Specifically, the 3-axis accelerometer may be used to detect PD 12 motion that may be indicative of cardiac events and/or noise. For example, processing circuitry 90 may monitor the accelerations from motion sensor 100 to confirm or detect arrhythmias. Since PD 12 may move with a chamber wall of heart 16, the detected changes in acceleration may also be indicative of contractions. Therefore, PD 12 may be configured to, based on the signal from sensor 100, identify heart rates and confirm ventricular dyssynchrony sensed via sensing circuitry 98.

When processing circuitry 90 controls therapy generation circuitry 96 to deliver ventricular pacing pulses for CRT, processing circuitry 90 may also control motion sensor(s) 100 to generate a signal that varies with the cardiac contraction. In some examples, motion sensor(s) 100 may generate the signal substantially continuously. For each cardiac cycle during which a ventricular pacing pulses is delivered, processing circuitry 90 may identify one or more features of the cardiac contraction within the signal. Processing circuitry 90 may determine whether the contraction is a fusion beat or other type of beat, e.g., intrinsic or fully-paced, based on the one or more features.

The one or more features of the cardiac contraction may comprise, as examples, one or more of a slope of the motion signal during the cardiac contraction, an amplitude of the motion signal during the contraction, a maximum of the signal during the cardiac contraction, a minimum of the signal during the cardiac contraction, a ratio of the maximum and the minimum during the cardiac contraction, or a polarity of the signal during the cardiac contraction. As described in greater detail below, such as with respect to FIGS. 11A and 11B, the one or more features of the cardiac contraction within the signal may comprise one or more of an amount or a direction of motion relative to a point of origin during the contraction. In some examples, the amount of motion is in at least one direction other than the primary axis of motion during the cardiac contraction, e.g., an amount of motion in at least one plane orthogonal to the primary axis of motion during the cardiac contraction. In some examples, the motion of interest may be radial motion in the plane orthogonal to the primary axis of motion during the cardiac contraction.

In examples in which one or more sensor(s) 100 are other than an accelerometer, the features used to evaluate the cardiac contraction using the techniques described herein may be the same or different than those provided by an accelerometer. For example, a gyroscope may provide rotational mechanical information different from that provided by accelerometers, but may similarly be used to evaluate contractions. For example, template signals or values may be determined based on such signals and compared to current signals or values.

During left-ventricular contraction of a relatively healthy heart, all left-ventricular walls shorten synchronously and with similar force. Such a contraction pulls the atrio-ventricular plane and the left-ventricular apex toward each other. The movement of the atrio-ventricular plane and the left-ventricular apex toward each other defines the primary axis of motion during the cardiac contraction.

In the case of a totally synchronous activation of all left-ventricular walls, there is a total force balance at the apex, and there is minimal or no resulting radial motion component of the apex. In contrast, during asynchronous contraction, "apical rocking" (e.g., movement of the apex during systole, first toward the free wall and later toward the septum) or other motion of the apex or other heart tissue in a direction orthogonal to the primary axis can be observed. Several studies have shown that observation of apical rocking is predictive of subsequent CRT response. Apical rocking has been measured by echocardiography. For example, from a "4-chamber view," the apex moves 5 mm towards the lateral or free wall of the left ventricle during systole. The 4-chamber view is a 2-dimensional standardized echocardiographic visualization of the heart. The 4-chamber view visualizes the heart from the apex of the (left) cardiac chamber. The visualization plane through the heart is directed from the apex of the heart in such a way, that all 4 cardiac chambers (right atrium, left atrium, right ventricle and left ventricle) are visualized at the same time.

Motion sensor(s) 100 being located at or near the apex, e.g., because PD 12 is implanted at that location, may be configured to detect apical rocking. However, motion sensor(s) 100 being implanted at other locations, e.g., on the ventricular free wall or septum, may also detect motion in a direction other than the primary axis of motion during the cardiac contraction. Further, motion sensor(s) 100 may detect motion or displacement in any radial direction away from the origin point of the cardiac cycle.

In some examples, the one or more the one or more features of the cardiac contraction within the signal comprise one or more values resulting from comparison of the signal during the cardiac contraction to one or more templates. Such values may include differences between the signal the template, which may be compared to thresholds to determine whether the signal "matches" the template, e.g., is sufficiently similar to the template. The one or more templates may be stored in memory 92 (or another memory of system 8). The one or more templates may be generated by processing circuitry 90 or other processing circuitry based on the motion signal during one or more previous beats of known classification (such as by averaging the signal for a plurality of known beats of a given classification), either of the particular patient, or from a population of one or more similar patients. The one or more templates may include one or more of an intrinsic beat template, a fully-paced beat template, or a fusion beat template, and processing circuitry may characterize a given contraction as the one of a fusion beat, intrinsic beat, or fully-paced beat whose template the signal best matches.

Further, the templates need not take the form of one or more substantially continuous-time signals, representing a number of values, from one or more sensors during a contraction (or portion of such a signal). Rather, a template may take the form of a template value for any one or more of the contraction features disclosed herein. The template value may, but need not necessarily be, determined based on a template signal or otherwise determined from motion signals collected during one or more previous beats of known classification (such as by averaging the signal for a plurality of known beats of a given classification), either of the particular patient, or from a population of one or more similar patients. Template values may include, as examples, values of: slope of the motion signal during the cardiac contraction, an amplitude of the motion signal during the contraction, a maximum of the signal during the cardiac contraction, a minimum of the signal during the cardiac contraction, a ratio of the maximum and the minimum during the cardiac contraction, a polarity of the signal during the cardiac contraction, or an amount of motion in one or more particular directions, such as orthogonal to the primary axis of motion, which may include apical rocking. The templates can include template values for multiple contraction features. Although described in the context of processing circuitry 90 of intracardiac PD 12, processing circuitry of any one or more devices described herein may similarly use templates to classify contractions.

Communication circuitry 94 includes any suitable hardware, firmware, software or any combination thereof for communicating with another device, such as external device 24 or IMD 10, via TCC or RF signals, as described herein. In some examples, communication circuitry 94 may be configured for TCC communication with IMD 10 via electrodes 52 and 60. PD 12 may communicate with external device 24 via IMD 10, or communication circuitry 94 may be configured for RF communication with external device 24, e.g., via an antenna. In some examples, PD 12 may signal external device 24 to further communicate with and pass the alert through a network such as the Medtronic CareLink® Network developed by Medtronic plc of Dublin, Ireland, or some other network linking patient 14 to a clinician. PD 12 may spontaneously transmit information to the network or in response to an interrogation request from a user.

There may be numerous variations to the configuration of PD 12, as described herein. In one example, PD 12 includes a housing configured to be implanted within heart 16 of patient 14, one or more electrodes (e.g., electrodes 52 and 60) coupled to the housing, fixation mechanism 62 configured to attach the housing to tissue of heart 16, sensing circuitry 98 configured to sense an electrical signal from heart 16 of patient 14 via the one or more electrodes, and signal generation circuitry 96 configured to deliver therapy to heart 16 of patient 14 via the one or more electrodes. PD 12 may also include processing circuitry 90 configured to receive a communication message from IMD 10 requesting PD 12 deliver CRT to heart 16, where IMD 10 is configured to be implanted exterior to a ribcage of patient 14. Processing circuitry 90 may also be configured to determine, based on the sensed electrical signal, whether to deliver CRT to heart 16, and, in response to the determination, command signal generation circuitry 96 to deliver the CRT therapy. For example, processing circuitry 90 may withhold delivery of CRT pacing pulse during a particular cardiac cycle if sensing circuitry 98 indicates detection of an intrinsic R-wave prior to expiration of a timing interval, e.g., an A-V interval. If processing circuitry 90 controls signal generation circuitry 96 to deliver the pacing pulse, processing circuitry 90 or other processing circuitry of one or more other devices may analyze the signal from motion sensor(s) 100 to classify the cardiac contraction as described herein.

Figure 7:
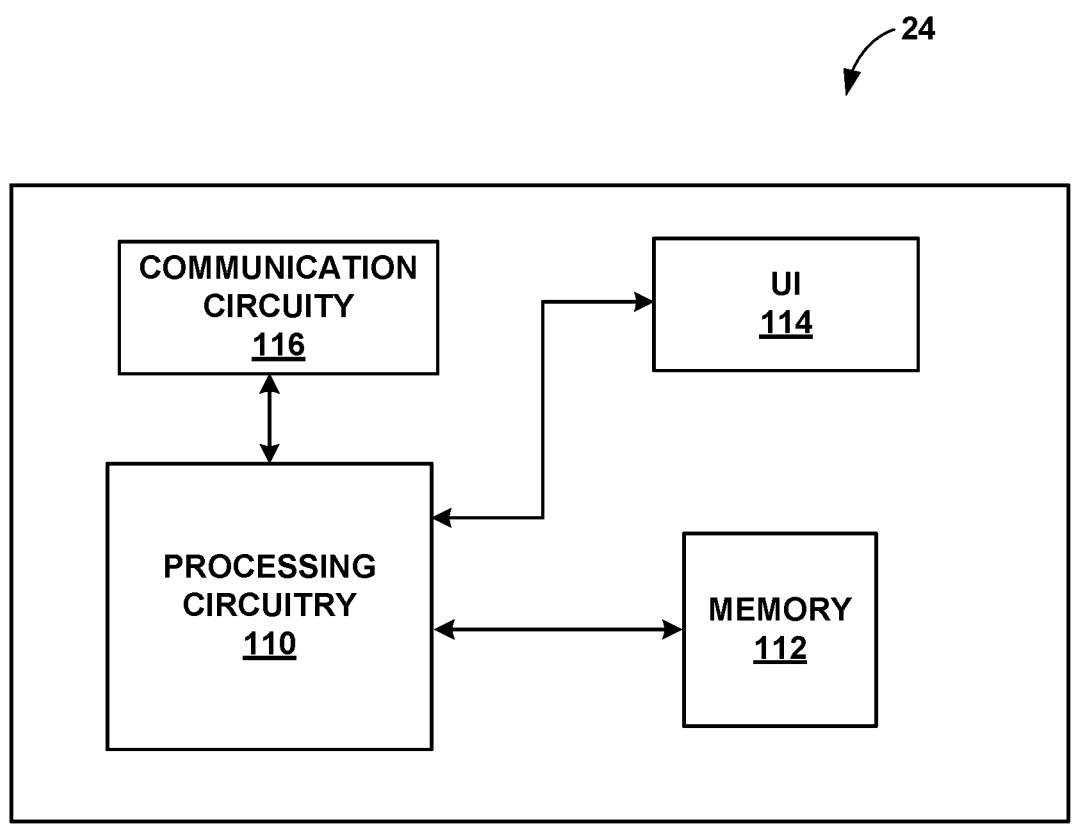
FIG. 7 is a functional block diagram illustrating an example configuration of the external device in FIG. 1A, in accordance with one or more aspects of this disclosure.

FIG. 7 is a functional block diagram illustrating an example configuration of external device 24. As shown in FIG. 7, external device 24 may include processing circuitry 110, memory 112, user interface 114, and communication circuitry 116. External device 24 may be a dedicated hardware device with dedicated software for communication with, e.g., programming of, PD 12 and/or IMD 10. Alternatively, external device 24 may be an off-the-shelf computing device running an application that enables external device 24 to program and/or otherwise communicate with PD 12 and/or IMD 10.

A user may use external device 24 to configure the operational parameters of and retrieve data from PD 12 and/or IMD 10. In one example, external device 24 may communicate directly to both PD 12 and IMD 10. In other examples, external device 24 may communicate to one of PD 12 and IMD 10, and that device may relay any instructions or information to or from the other device. The clinician may interact with external device 24 via user interface 114, which may include display to present graphical user interface to a user, and a keypad or another mechanism for receiving input from a user. In addition, the user may receive an alert or notification from IMD 10 indicating that a shock has been delivered, any other therapy has been delivered, or any problems or issues related to the treatment of patient 14.

Processing circuitry 110 can take the form one or more microprocessors, DSPs, ASICs, FPGAs, programmable logic circuitry, or the like, and the functions attributed to processing circuitry 110 herein may be embodied as hardware, firmware, software or any combination thereof. Memory 112 may store instructions that cause processing circuitry 110 to provide the functionality ascribed to external device 24 herein, and information used by processing circuitry 110 to provide the functionality ascribed to external device 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before external device 24 is used to program therapy for another patient.

External device 24 may communicate wirelessly with PD 12 and/or IMD 10, such as using RF communication or proximal inductive interaction. This wireless communication is possible with communication circuitry 116, which may be coupled to an internal antenna or an external antenna. An external antenna that is coupled to external device 24 may correspond to the programming head that may be placed over heart 16 or the location of the intend implant, as described above with reference to FIG. 1. Communication circuitry 116 may be configured with circuitry like communication circuitry 78 of FIG. 5.

Communication circuitry 116 may also be configured to communicate with another computing device via wireless communication techniques, or direct communication through a wired connection. Examples of local wireless communication techniques that may be employed to facilitate communication between external device 24 and another computing device include RF communication according to the 802.11 or Bluetooth specification sets, infrared communication, e.g., according to the IrDA standard, or other standard or proprietary telemetry protocols. An additional computing device in communication with external device 24 may be a networked device such as a server capable of processing information retrieved from IMD 10 and/or PD 12.

In some examples, processing circuitry 110 may receive a signal from sensor 100 of PD 12 via direct or indirect communication with PD 12 using communication circuitry 116. using the signal, processing circuitry 110 may, in whole or in part, perform any of the methods described herein for adapting and evaluating CRT, including one or more of classifying beats as fusion or other based on the signal, controlling a timing interval or other control parameter value used by IMD 10 and/or PD 12 for timing the delivery of CRT by PD 12 based on the classification of the beats, and determining values of one or more metrics indicating an amount of beats that were fusion beats and, thus, the effectiveness of CRT. In some examples, processing circuitry 110 may receive values for features of contractions rather than the motion signal, or classifications of beats rather than the feature values, and perform some portions of methods described herein using the received features or classification information.

Figure 8:
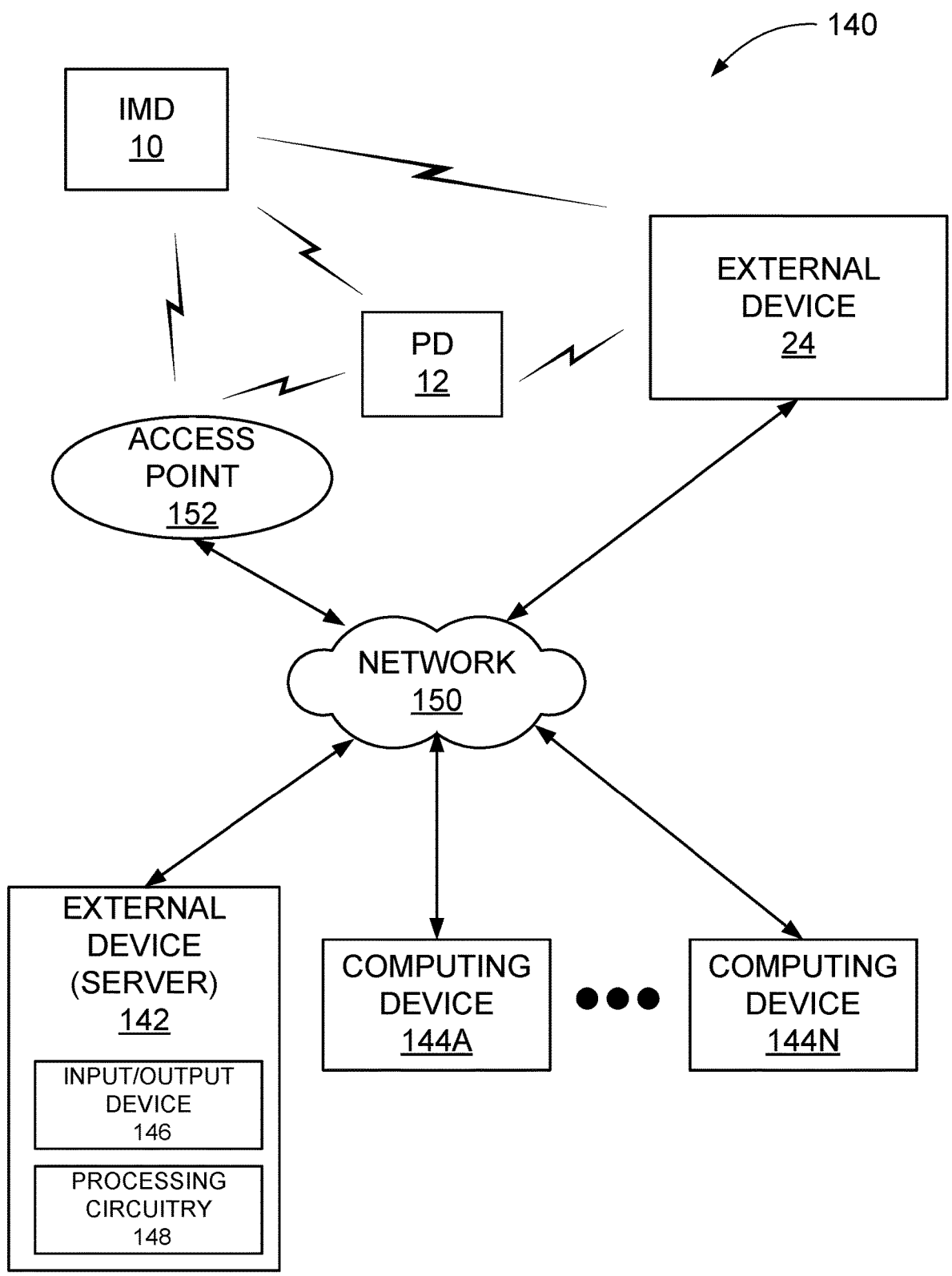
FIG. 8 is a block diagram illustrating a system that includes an external device, such as a server, and one or more computing devices that are coupled to an IMD, PD, and external device via a network, in accordance with one or more aspects of this disclosure.

FIG. 8 is a block diagram illustrating a system 140 that includes an external device 142, such as a server, and one or more computing devices 144A-144N that are coupled to IMD 10, PD 12, and external device 24 via a network 150, according to one example. In this example, IMD 10 uses communication circuitry to communicate with external device 24 via a first wireless connection and communicates with an access point 152 via a second wireless connection. PD 12 uses communication circuitry to communicate with external device 24 via a first wireless connection and communicates with an access point 152 via a second wireless connection. IMD 10 and PD 12 communicate with each other via a shared third wireless connection. In the example of FIG. 8, access point 152, external device 24, external device 142, and computing devices 144A-144N are interconnected, and able to communicate with each other, through network 150. In some cases, one or more of access point 152, external device 24, external device 142, and computing devices 144A-144N may be coupled to network 150 through one or more wireless connections. IMD 10, PD 12, external device 24, external device 152, and computing devices 144A-144N may each comprise one or more processing circuitries, such as one or more microprocessors, DSPs, ASICs, FPGAs, programmable logic circuitry, or the like, that may perform various functions and operations, such as those described herein.

Access point 152 may comprise a device that connects to network 150 via any of a variety of connections, such as telephone dial-up, digital subscriber line (DSL), or cable modem connections. In other examples, access point 152 may be coupled to network 150 through different forms of connections, including wired or wireless connections. In some examples, access point 152 may communicate with external device 24, PD 12, and/or IMD 10. Access point 152 may be co-located with patient 14 (e.g., within the same room or within the same site as patient 14) or may be remotely located from patient 14. For example, access point 152 may be a home monitor located in the patient's home or is portable for carrying with patient 14.

During operation, IMD 10 and/or PD 12 may collect, measure, and store various forms of diagnostic data. For example, IMD 10 and/or PD 12 may collect EGM and motion signals, and determine different CRT configurations and A-V intervals. In certain cases, IMD 10 and/or PD 12 may directly analyze collected diagnostic data and generate any corresponding reports or alerts. In some cases, however, IMD 10 and/or PD 12 may send diagnostic data to external device 24, access point 152, and/or external device 142, either wirelessly or via access point 152 and network 150, for remote processing and analysis. For example, IMD 10 and/or PD 12 may send external device 24 data that indicates whether a loss of intrinsic AV conduction or CRT capture (fusion) was detected. External device 24 may generate reports or alerts after analyzing the data.

In another example, IMD 10 and/or PD 12 may provide external device 142 with collected EGM and motion signal data, system integrity indications, and any other relevant physiological or system data via access point 152 and network 150. External device 142 includes one or more processing circuitries 148. In some cases, external device 142 may request such data, and in some cases, IMD 10 and/or PD 12 may automatically or periodically provide such data to external device 142. Upon receipt of the diagnostic data via input/output device 146, external device 142 can analyze the data and generate reports or alerts upon determination that there may be a possible need for changed CRT parameters, or to indicate effectiveness of CRT.

In one example, external device 142 may comprise a secure storage site for information that has been collected from IMD 10, PD 12, and/or external device 24. In this example, network 150 may comprise an Internet network; and trained professionals, such as clinicians, may use computing devices 144A-144N to securely access stored data on external device 142. For example, the trained professionals may need to enter usernames and passwords to access the stored information on external device 142. In one embodiment, external device 142 may be a Medtronic CareLink® server provided by Medtronic plc of Dublin, Ireland.

In some examples, processing circuitry and memory of one or more of access point 152, server 142, or computing devices 144, e.g., processing circuitry 148 and memory of server 142, may be configured to provide some or all the functionality ascribed to processing circuitry and memory of IMD 10 and/or PD 12. For example, server 142 may be configured to receive a signal from sensor 100 of PD 12 via communication with PD 12 via network 150 and one or more of access point 152 and external device 234. Using the signal, processing circuitry 146 may, in whole or in part, perform any of the methods described herein for adapting and evaluating CRT, including one or more of classifying beats as fusion or other beats based on the signal, controlling a timing interval or other control parameter value used by IMD 10 and/or PD 12 for timing the delivery of CRT by PD 12 based on the classification of the beats, and determining values of one or more metrics indicating an amount of beats that were fusion beats and, thus, the effectiveness of CRT. External device 142 may communicate updated values for a timing interval that controls ventricular pacing pulse timing for CRT to IMD 10 and/or PD 12 via network 150. In some examples, such communication to IMD 10 and/or PD 12 may be after presentation of updated values to a clinician for approval via a computing device 144. In some examples, processing circuitry 148 of external device 142 may determine values of one or more metrics indicating effectiveness of CRT using the techniques described herein, or otherwise report such values to a clinician via a computing device 144. In some examples, processing circuitry 148 may receive features of contractions rather than the motion signal, or classifications of beats rather than the features, and perform some portions of methods described herein using the received features or classification information.

Figure 9:
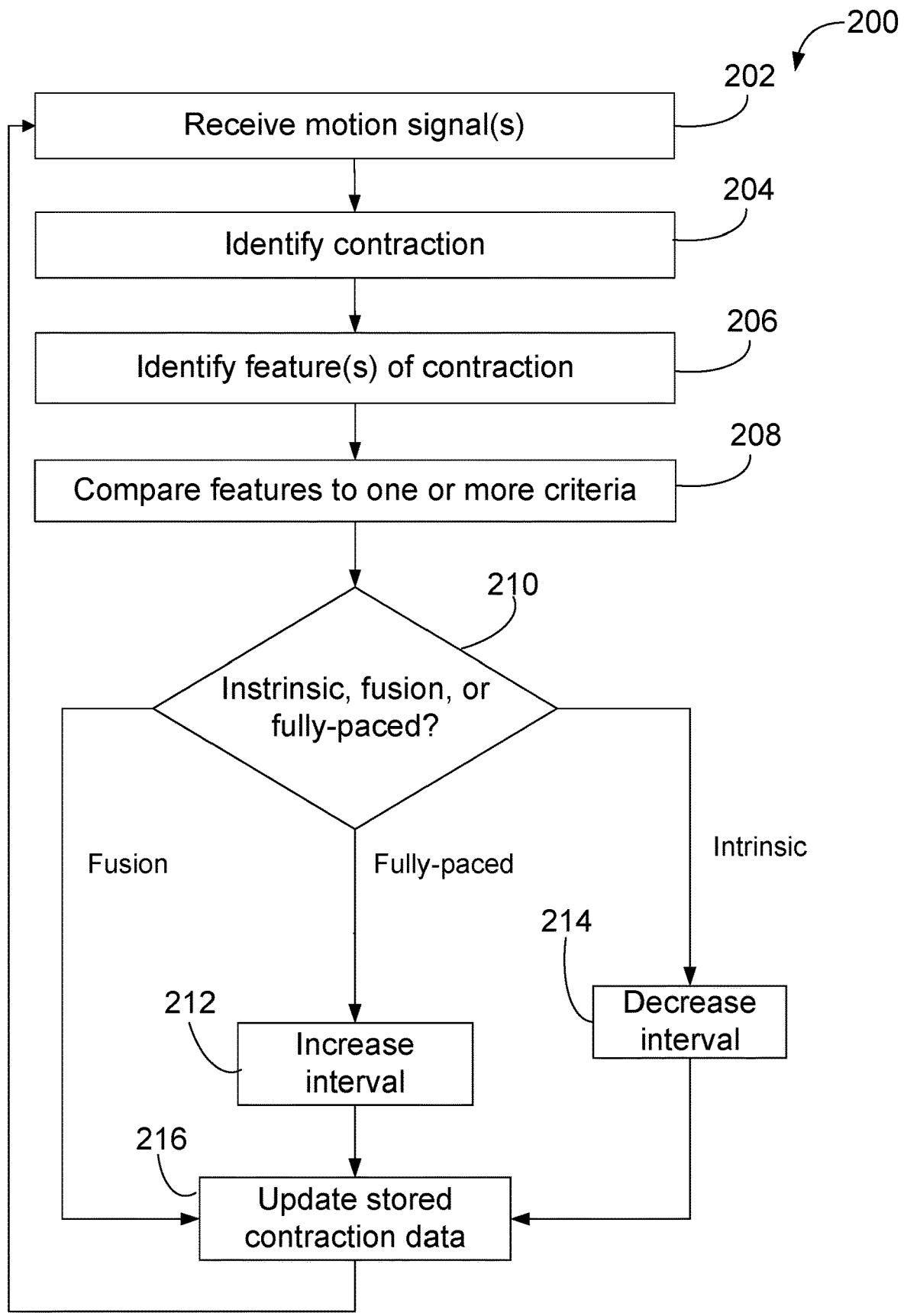
FIG. 9 is a flow diagram illustrating an example process delivering, evaluating, and adjusting cardiac resynchronization therapy through a PD, in accordance with one or more aspects of this disclosure.

FIG. 9 is a flow diagram illustrating an example process for delivering CRT through a PD 12, in accordance with one or more aspects of this disclosure. FIG. 8 illustrates method 200 in which CRT, such as fusion pacing, is delivered to cardiac tissue through PD 12, in communication with IMD 10, to address ventricular dyssynchrony present in a patient. Method 200 begins during or after IMD 10 and PD 12 are implanted into the patient. Method 200 may use IMD 10 and PD 12 in a master-slave communication mode, but other communication means can be applied as well. Additionally, method 200 is not limited to the examples in which PD 12 is affixed to an inner wall of the left ventricle and is in wireless communication with IMD 10. Other configurations can be used. For example, the RV can undergo fusion pacing instead of the LV. Additionally, PD 12 can be placed on an outer wall of the LV and/or RV. Furthermore, although described in the context of an example in which PD 12, and processing circuitry 90 of PD 12 perform a number of the functions illustrated in the example of FIG. 9, in other examples one or more of these functions may be performed by one or more other devices that communicate with PD 12, such as IMD 10, external device 24, external device 142, or computing devices 144, e.g., by the processing circuitry of such devices.

According to example method 200, the motion signal is received by processing circuitry 90 of PD 12 from sensor 100, which may be an accelerometer or gyroscope, as examples (202). Again, as discussed herein, the motion signal may be received by processing circuitry of other devices, including but not limited to IMD 10, external device 24, external device 142, and computing devices 144. The processing circuitry at such devices can receive the motion signal. Further, the motion signal may be more than one motion signal, e.g., a signal for each of a two or more axis of a multi-axis accelerometer, in some examples.

Processing circuitry 90 identifies a contraction within the motion signal (204), and identifies features of the contraction (206). The contraction may be identified based on identification of certain amplitudes in an expected timing relationship to a delivered ventricular pacing pulse. Features of the contraction may include, for example, an amount or magnitude of motion or displacement in a direction, such as in a plane orthogonal to the primary axis of motion during the contraction. In some examples, the amount of motion is characterized by a sum of the distances, at various points in time during the contraction, from a point of origin of the contraction, or by a maximum distance or another one or more distances from the point of origin. Example features of a contraction signal are illustrated and described in further detail with respect to FIG. 12.

Processing circuitry 90 compares the identified features of the contraction to one or more criteria, which may include comparison to one or more template values of the feature, as described herein (208). Based on the comparison, processing circuitry 90 may classify the contraction as a fusion beat, or another beat. In the illustrated example, processing circuitry 90 characterizes the contraction as one of a fusion beat, fully-paced beat, or intrinsic beat (210). PD 12 can assess the cardiac contraction after each pace and use this for subsequent optimization of pace timing.

A fully-paced beat may refer to a beat in which the ventricular pacing pulse delivered to one ventricle captured the other ventricle, rather than fusing with the intrinsic depolarization from the other ventricle. A fully-paced beat suggests that the pacing pulse was delivered too early. In response to classification of a contraction as a fully-paced beat, processing circuitry may increase a timing interval for the CRT pacing, e.g., an A-V interval, such as an A-LV interval (212). In other examples, in response to classification of a contraction as a fully-paced beat, processing circuitry may decrease the degree of pre-excitation of the LV in a manner other than by increasing an A-LV interval, such as by decreasing a V-V interval. For example, processing circuitry may increase an A-V interval by about 10 ms, or decrease a V-V interval by about 10 ms.

The occurrence of an intrinsic beat after delivery of a ventricular pacing pulse for CRT (also referred to as pseudofusion), suggests that the pacing pulse was delivered too late. Pseudo-fusion involves electrical activation of the cardiac tissue almost entirely through intrinsic electrical activity with minimal or no contribution from pacing. While fusion is typically characterized by a wave complex formed by depolarization of the myocardium initiated by two different foci, commonly a non-native stimulus as from a PD and a native stimulus, pseudofusion is typically characterized by a wave complex formed by depolarization of the myocardium initiated by a native stimulus; however, a non-native stimulus, that does not contribute to depolarization, adds a pacing artifact on top of the native wave complex.

Pseudofusion happens when a pacing pulse is coincident with a spontaneous QRS complex during ventricular pacing. If the tissue around the electrode has already spontaneously depolarized and is in its refractory period, the pacing stimulus may be ineffective. Techniques for detecting pseudofusion beats based on the cardiac EGM have been proposed. However, according to the techniques of this disclosure, pseudofusion beats may be detected based on one or more features of a motion signal.

In response to classification of a contraction as an intrinsic beat, processing circuitry may decrease a timing interval for the CRT pacing, e.g., an A-V interval, such as an A-LV interval (214). In other examples, in response to classification of a contraction as an intrinsic beat, processing circuitry may increase the degree of pre-excitation of the LV in a manner other than by decreasing an A-LV interval, such as by increasing a V-V interval. For example, processing circuitry may decrease an A-V interval by about 10 ms, or increase a V-V interval by about 10 ms. In some examples, such as those in which biventricular pacing is delivered, a V-V interval may be maintained and adjusted as described herein. For example, if there is delayed conduction near the LV pacing location, the paced RV activation will dominate paced LV activation (e.g., resulting in insufficient fusion) unless the LV is given a "head start." In this case, the V-V delay may be set and modified to pre-excite the LV.

Although not illustrated in FIG. 9, processing circuitry 90 may also decrease the timing interval (or otherwise increase the degree of pre-excitation of a ventricle) based on receiving an R-wave indication from sensing circuitry 98 and withholding the delivery of a pacing pulse. The decrease may be the same as, or different than, the decrease applied when a pacing pulse is delivered by the contraction is classified as intrinsic. For example, processing circuitry may decrease an A-V interval by about 10 ms (or increase a V-V interval by about 10 ms). As illustrated by FIG. 9, processing circuitry 90 may leave the timing interval unchanged based on classifying the contraction as a fusion beat.

As illustrated in the example of FIG. 9, processing circuitry 90 may also update contraction data, e.g., stored in memory 92, based on the classification of the contraction (216). The contraction data may include values for one or more metrics that indicate an effectiveness of CRT, such as a percentage or other amount of paced cardiac cycles that result in fusion beats. In various examples, the stored cardiac contraction data can be at several locations including but not limited to IMD 10, PD 12, external device 24, external device 152, and computing devices 144A-144N. In some examples, the stored contraction data may be provided to external device 24, external device 142, or computing devices 144 for presentation to a user.

The example method of FIG. 9 may be performed on a beat-to-beat basis, e.g., for each cardiac cycle for which PD 12 delivers a pacing pulse, or less frequently, such as according to a X of Y cycle or X cycle every time period schedule, or in response to an instruction from a user. For example, the method of FIG. 9 may be performed for one cycle out of every ten cycles, or for one cycle every minute.

In other examples, the method of FIG. 9 may be performed in response to detection of atrial fibrillation (AF), e.g., by IMD 10. During AF in patients with intact AV conduction, random impulses passed through the AV node result in chaotic activation timing of the ventricles. As a result, it is very difficult to maintain consistent pace timing and high-quality CRT during AF. In certain examples, IMD 10 monitors for P-waves and commands PD 12 to pace at the right times. When AF begins, IMD 10 detects the AF and could communicate to PD 12 that the patient is in AF. In response to the communication, PD 12 may begin the example method of FIG. 9, including analysis of the motion signal, to maintain effective pacing timing and capture for CRT during AF.

In examples in which AF is detected, pacing may switch from an atrial tracking mode to a non-atrial tracking mode. In a non-atrial tracking mode, the timing interval used to control the delivery of ventricular pacing is an escape interval from a paced or intrinsic ventricular depolarization of the preceding cardiac cycle. In examples in which the atrial synchronous ventricular pacing is delivered by an intracardiac PD 12 based signals from IMD 10, IMD 10 may stop sending and/or PD 12 may ignore such signals in response to AF.

The method of FIG. 9 may be performed during AF, but increasing (212) or decreasing (214) an interval may refer to the escape interval. An example amount to increase or decrease the escape interval during AF is between about 10 ms and about 50 ms. In this scenario, processing circuitry could also increase the escape interval by a relatively small amount, e.g., about 10 ms, in response to detection of a fully paced beat (212) to avoid pacing too fast.

In some examples, medical device system 8 is a cardiac resynchronization therapy defibrillator (CRT-D) system that comprises an EV-ICD as IMD 10 and an LV pacing device as PD 12. The EV-ICD senses P-waves and communicates timing of the P-wave to the LV pacing device, which determines the best A-V delay for pacing. If the selected A-V delay was too long, the LV pacing device can sense intrinsic depolarization (e.g., a sensed event) or can determine through the accelerometers that pseudofusion has occurred. This implies that future A-V intervals need to be foreshortened. The LV pacing device can automatically adjust timing intervals to achieve the longest A-V interval that avoids pseudofusion or sensed events, thus maintaining fusion. In some examples, the pacing device could also discriminate A-V intervals that are too short by observing a fully-paced accelerometer pattern, rather than an optimal fusion accelerometer pattern. This would imply the need to increase future A-V intervals. This method avoids the skipping of occasional paced beats, uses direct measurement of mechanical contraction, and can adjust A-V intervals each beat.

In another example, PD 12 may not be able to determine if effective capture occurs based on its LV EGM (the EGM from the pacing device is near-field whereas far-field EGM may better assess effective capture). However, PD 12 is equipped with motion sensor 100, such as a three-dimensional accelerometer or gyroscope. The accelerometer provides feedback about the mechanical contraction pattern. The pacing device can learn the accelerometer pattern for an intrinsic beat and separately for an effective capture beat. During AF, if the pacing device delivers a pace but sees an intrinsic accelerometer pattern, this suggests that pseudofusion occurred and suggests the need to increase the pacing rate to overdrive AF conduction. If the pacing device senses an intrinsic ventricular activation, this also suggests the need to increase the pacing rate. Alternatively, if the pacing device senses an effective capture beat (via accelerometers) following a pace, this suggests that effective capture is occurring, and the future pacing rate could be decreased a small amount, to avoid pacing too rapidly. This beat-by-beat assessment and adjustment of pacing rate will result in maximal effective capture during AF while attempting to minimize the pacing rate.

While method 200 is described relative to PD 12 placed in the left ventricle, skilled artisans appreciate that the present disclosure can be applied to many different embodiments in which IMD 10 is used in combination with PD 12. For example, PD 12 can be implanted within a chamber of the heart or substernally/retrosternally, as described in U.S. provisional patent application Ser. No. 61/819,946 filed May 6, 2013 and entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE", incorporated by reference in its entirety, U.S. provisional patent application Ser. No. 61/820,024 filed May 6, 2013 and entitled "ANCHORING AN IMPLANTABLE MEDICAL DEVICE WITHIN A SUB STERNAL SPACE", and U.S. provisional patent application Ser. No. 61/820,014 filed May 6, 2013 and entitled "SYSTEMS AND METHODS FOR IMPLANTING A MEDICAL ELECTRICAL LEAD WITHIN A SUBSTERNAL SPACE", all of which are incorporated by reference herein. The IMD is configured to deliver shocks to the patient without any leads implanted within the vasculature and/or heart of the patient.

Figure 10:
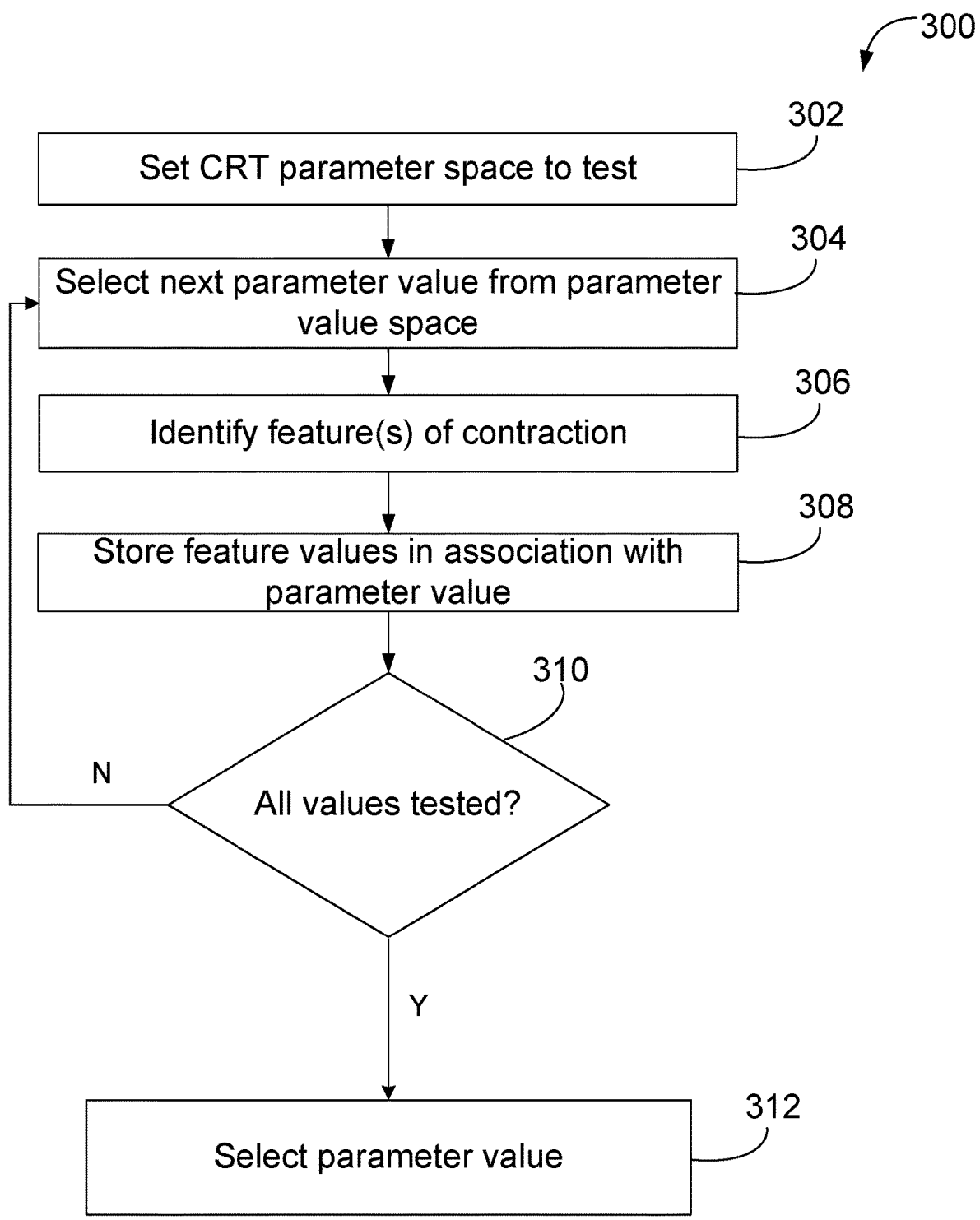
FIG. 10 is a flow diagram illustrating an example process for determining parameter values for cardiac resynchronization therapy based on an evaluation of one or more cardiac contraction features, in accordance with one or more aspects of this disclosure.

FIG. 10 is a flow diagram illustrating an example process for determining parameter values for cardiac resynchronization therapy based on an evaluation of one or more cardiac contraction features. Method 300 may use IMD 10 and PD 12 in a master-slave communication mode, but other communication means can be applied as well. Additionally, similar to method 200, method 300 is not limited to the examples in which PD 12 is affixed to an inner wall of the left ventricle and is in wireless communication with IMD 10. Other configurations may be used as discussed with method 200 in FIG. 9. Furthermore, although described in the context of an example in which PD 12 and processing circuitry 90 of PD 12 perform a number of the functions illustrated in the example of FIG. 10, in other examples one or more of these functions may be performed by one or more other devices that communicate with PD 12, such as IMD 10, external device 24, external device 142, or computing devices 144, e.g., by the processing circuitry of such devices.

FIG. 10 illustrates an example method for testing a plurality of values of one or more CRT control parameters while monitoring the contractions resulting from delivery of CRT according to different parameter values using the techniques described herein. The value(s) of the CRT control parameter(s) that provide desired contractions, e.g., desired values of one or more contraction features, may be selected for ongoing delivery of CRT therapy. The example method of FIG. 10 may be performed shortly after implant of a system 8, at a clinic visit, and/or automatically in response to a remote command or on a periodic basis.

According to the example of FIG. 10, values (such as ranges of values) for one or more parameters, including, e.g., AV-delay, VV-delay, and pacing configuration will be selected to form a CRT parameter space to test (302). Once the parameter space has been established, a parameter value from the parameter value space will be tested (304).

Similar to step 206 in FIG. 9, processing circuitry 90 identifies features of the contraction (306). The contraction may be identified based on identification of certain amplitudes in an expected timing relationship to a delivered ventricular pacing pulse. Features of the contraction may include, for example, an amount or magnitude of motion or displacement in a direction, such as in a plane orthogonal to the primary axis of motion during the contraction. In some examples, the amount of motion is characterized by a sum of the distances, at various points in time during the contraction, from a point of origin of the contraction, or by a maximum distance or another one or more distances from the point of origin. Example features of a contraction signal are illustrated and described in further detail with respect to FIG. 12.

Processing circuitry 90 stores feature values in association with the parameter value that has been selected from the parameter values space, as described herein (308). The values may either be stored locally, used in closed-loop fashion to adjust the timing directly, or communicated by wire or wirelessly to some sort of control unit.

If all values have not been tested (310), the method may return to the beginning of the method at step 304 and select the next parameter value from the parameter value space. Once all of the parameters from the parameter value space have been tested (310), the parameter value with desired contraction feature value(s), e.g., with minimal radial displacement, may be selected (312).

Although the example techniques of FIGS. 9 and 10 are described primarily in the context of a PD 12 implanted in the left-ventricle, other example medical devices may implement the techniques to evaluate the effectiveness of CRT control parameter values. For example, an extracardiac pacemaker may deliver ventricular pacing through electrodes of one or more leads. The pacemaker may also be coupled to a motion sensor, e.g., by a lead or wirelessly, to receive a motion signal during cardiac contraction.

Figure 11A:
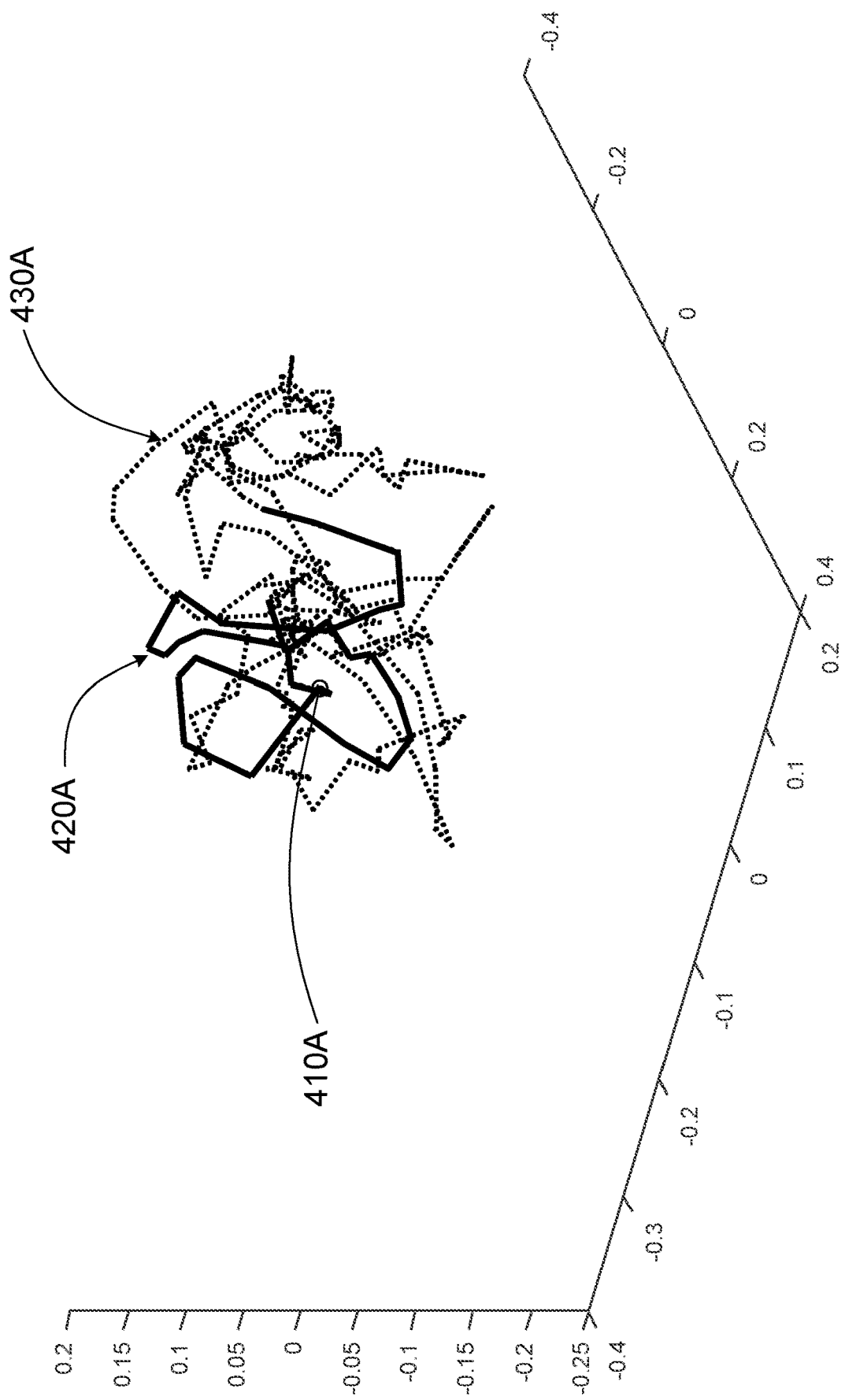
FIG. 11A is a plot illustrating cardiac motion during normal sinus rhythm (NSR, intrinsic beat) looking down the systolic axis, in accordance with one or more aspects of this disclosure.
Figure 11B:
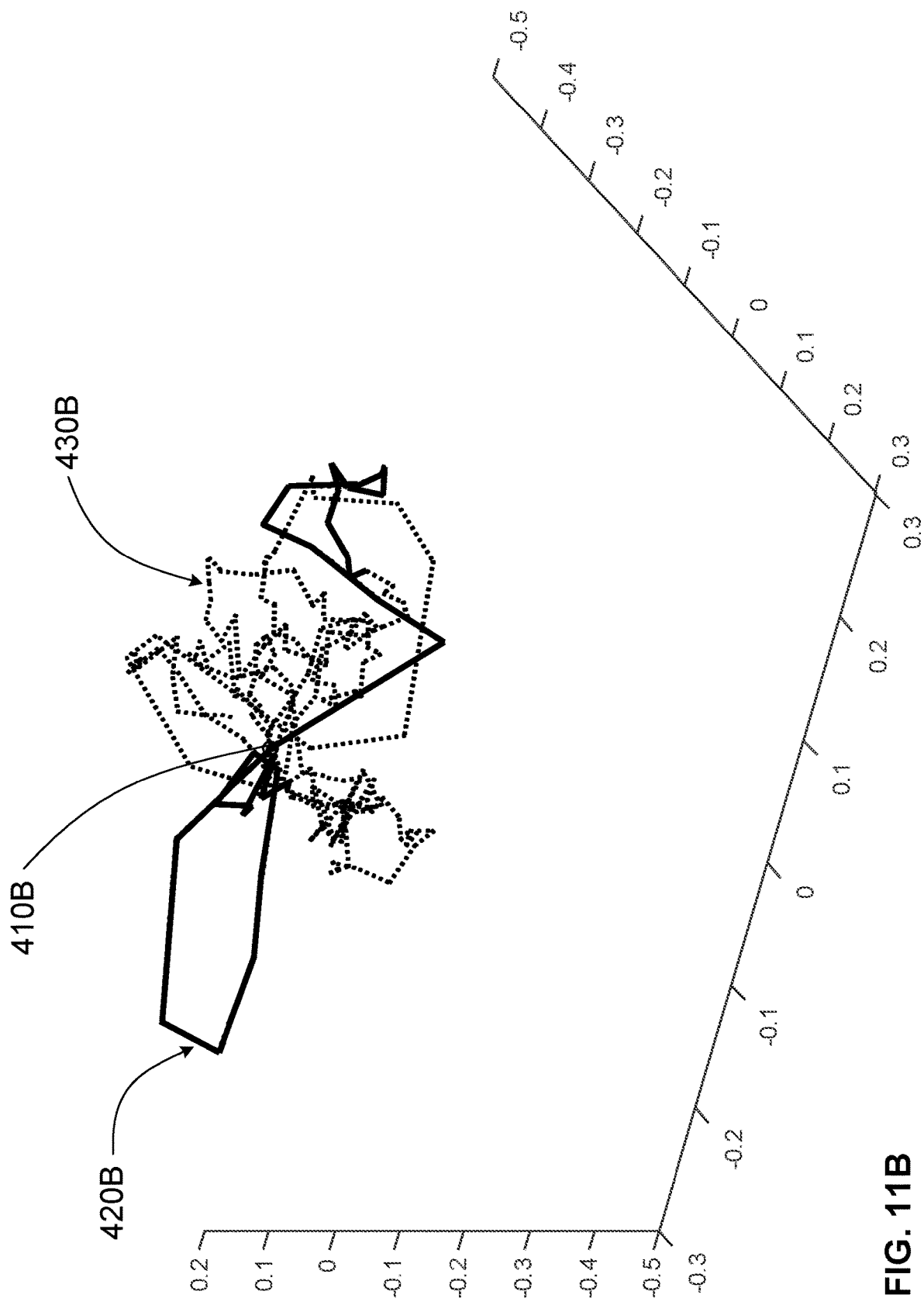
FIG. 11B is a plot illustrating cardiac motion during right ventricular (RV) pacing looking down the systolic axis, in accordance with one or more aspects of this disclosure.

FIGS. 11A and 11B show actual human three-dimensional accelerometer data (in units where 1=the gravitational force of Earth) from a pacing device. FIG. 11A is a plot illustrating normal sinus rhythm (NSR, intrinsic beat) looking down the systolic axis. The axes have been transformed from the accelerometer axes of the pacing device, such that the primary axis of systolic contraction is now along an axis that points out of the plane of the image. The plane of the image thus shows the accelerometer components that are orthogonal to the primary systolic contraction. FIG. 11B is a plot illustrating right ventricular (RV) pacing looking down the systolic axis. FIGS. 11A and 11B each show one cardiac cycle. In FIG. 11A, a point of origin of the contraction is identified with reference item number 410A, a systole portion of the cardiac cycle is identified with reference item number 420A, and the diastole portion of the cardia cycle is identified with reference item number 430A. In FIG. 11B, a point of origin of the contraction is identified with reference item number 420B, the systole portion of the cardiac cycle is identified with reference item number 420B, and a diastole portion of the cardiac cycle is identified with reference number 430B. FIG. 11B shows that the RV paced beat has greater systolic motion in this orthogonal plane than FIG. 11A (the intrinsic (NSR) beat) because the RV paced beat causes dyssynchronous contraction. By determining an amount of motion in a direction other than the primary axis of systolic contraction, such as in a plane orthogonal to the axis, the degree of dyssynchrony can be estimated. In some examples, the amount of motion may be a sum of distances from an origin at various points during the systole portion of the cardiac cycle. The amount of dyssynchronous motion may be used, according to the techniques of this disclosure to discriminate fusion (A-V interval satisfactory) from other types of beats, such as intrinsic depolarization (A-V interval too long) and fully LV paced beats (A-V interval too short).

Figure 12:
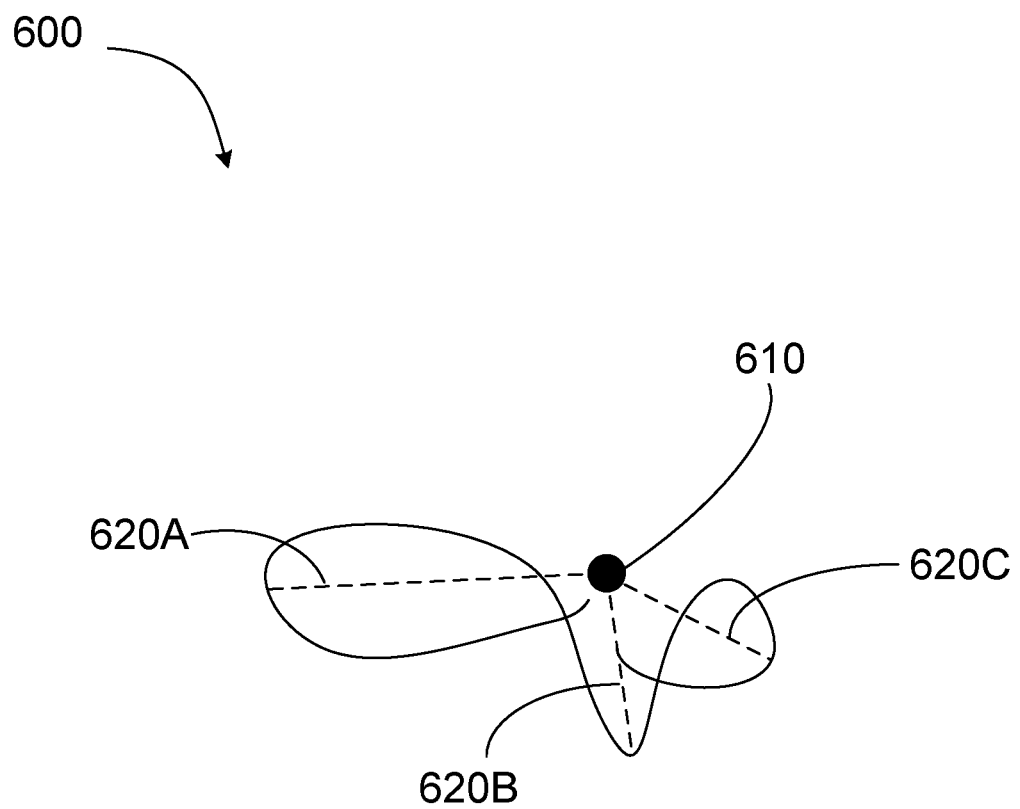
FIG. 12 is a plot of cardiac motion illustrating example features of a cardiac motion signal, in accordance with one or more aspects of this disclosure.

FIG. 12 is a conceptual plot of cardiac motion illustrating example features of a cardiac motion signal, in accordance with one or more aspects of this disclosure. FIG. 12 shows a plot illustrating an example of one systolic portion 600 of a cardiac cycle looking down the primary systolic axis of motion. Vectors 620A, 620B, and 620C (collectively "vectors 620") illustrate motion or displacement from an origin of the contraction 610 in directions other than along the primary systolic axis, e.g., radial motion in a plane orthogonal to the primary axis, such as due to apical rocking. Although three vectors 620 are illustrated in FIG. 12, processing circuitry may determine more or fewer vectors 620 to determine a feature of a cardiac contraction as described herein. FIG. 12 shows the beat having a large systolic motion with a vector 620A from origin of the contraction 610. The amount of motion in a direction other than the primary axis of systolic contraction, e.g., the maximum, sum, or mean of vectors 620, may be used to estimate the degree of dyssynchrony, e.g., as a value of a feature of a cardiac contraction. Vectors, such as vectors 620B and 620C, with short distances to origin of the contraction 610 may be used to indicate the absence of a dyssynchronous contraction. While vectors, such as vector 620A, with large distances origin of the contraction 610 may indicate a dyssynchronous contraction.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

In addition, it should be noted that system described herein may not be limited to treatment of a human patient. In alternative examples, the system may be implemented in non-human patients, e.g., primates, canines, equines, pigs, and felines. These other animals may undergo clinical or research therapies that may benefit from the subject matter of this disclosure.

The techniques described in this disclosure, including those attributed to IMD 10, PD 12, external device 24, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between IMD 10, PD 12, external device 24. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

Various examples have been described. These and other examples are within the scope of the following claims.

What is claimed is:

1. A system for delivering cardiac resynchronization therapy, the system comprising:
   a pacing device comprising a housing configured for implantation within a heart of a patient, the pacing device further comprising:
   a plurality of electrodes;
   signal generation circuitry within the housing, the signal generation circuitry configured to deliver ventricular pacing via the plurality of electrodes; and
   a sensor within the housing configured to produce a signal that indicates mechanical activity of the heart; and
   processing circuitry configured to:
   identify one or more features of a cardiac contraction within the signal;
   determine whether the cardiac contraction is a fusion beat based on the one or more features; and control a timing interval for delivery of the ventricular pacing based on the determination.

2. The system of claim 1, wherein the one or more features of the cardiac contraction within the signal comprise one or more of a slope of the signal during the cardiac contraction, an amplitude of the signal during the contraction, a maximum of the signal during the cardiac contraction, a minimum of the signal during the cardiac contraction, a ratio of the maximum and the minimum during the cardiac contraction, or a polarity of the signal during the cardiac contraction.

3. The system of claim 1, wherein the one or more features of the cardiac contraction within the signal comprise one or more of an amount or a direction of motion relative to a point of origin during the contraction.

4. The system of claim 3, wherein the one or more features of the cardiac contraction within the signal comprise an amount of motion in at least one direction other than the primary axis of motion during the cardiac contraction.

5. The system of claim 3, wherein the one or more features of the cardiac contraction within the signal comprise an amount of motion in at least one plane orthogonal to the primary axis of motion during the cardiac contraction.

6. The system of claim 1, wherein the one or more features of the cardiac contraction within the signal comprise one or more values resulting from comparison of the signal during the cardiac contraction to one or more templates.

7. The system of claim 6, wherein the one or more templates comprise one or more of an intrinsic beat template, a fully-paced beat template, or a fusion beat template.

8. A method for delivering cardiac resynchronization therapy by a pacing device comprising a housing configured to be implanted within a heart of a patient, the method comprising, by processing circuitry of a medical device system comprising the pacing device:
    receiving a signal from a sensor within the housing of the pacing device, the signal indicating mechanical activity of the heart;
    identifying one or more features of a cardiac contraction within the signal;
    determining whether the cardiac contraction is a fusion beat based on the one or more features; and
    controlling a timing interval for delivery of ventricular pacing by signal generation circuitry within the housing of the pacing device based on the determination.

9. The method of claim 8, wherein the one or more features of the cardiac contraction comprise one or more of a slope of the signal during the cardiac contraction, an amplitude of the signal during the contraction, a maximum of the signal during the cardiac contraction, a minimum of the signal during the cardiac contraction, a ratio of the maximum and the minimum during the cardiac contraction, and a polarity of the signal during the cardiac contraction.

10. The method of claim 8, wherein the one or more features of the cardiac contraction within the signal comprise one or more of an amount or a direction of motion relative to a point of origin during the contraction.

11. The method of claim 10, wherein the one or more features of the cardiac contraction within the signal comprise an amount of motion in at least one direction other than the primary axis of motion during the cardiac contraction.

12. The method of claim 10, wherein the one or more features of the cardiac contraction within the signal comprise an amount of motion in at least one plane orthogonal to the primary axis of motion during the cardiac contraction.

13. The method of claim 8, wherein the one or more features of the cardiac contraction within the signal comprise one or more values resulting from comparison of the signal during the cardiac contraction to one or more templates.

14. The method of claim 13, wherein the one or more templates comprise one or more of an intrinsic beat template, a fully-paced beat template, or a fusion beat template.

15. A system comprising:
    means for receiving a signal from a sensor within a housing of a pacing device, the housing being configured for implantation within a heart of a patient, the signal indicating mechanical activity of the heart;
    means for identifying one or more features of a cardiac contraction within the signal;
    means for determining whether the cardiac contraction is a fusion beat based on the one or more features; and
    means for controlling a timing interval for delivery of ventricular pacing by signal generation circuitry within the housing of the pacing device based on the determination.

16. A computer-readable storage medium comprising instructions that, when executed by processing circuitry of a medical device system comprising a pacing device comprising a housing configured for implantation within a heart of a patient, cause the processing circuitry to:
    receive a signal from a sensor within the housing of the pacing device, the signal indicating mechanical activity of the heart of the patient;
    identify one or more features of a cardiac contraction within the signal;
    determine whether the cardiac contraction is a fusion beat based on the one or more features; and
    control a timing interval for delivery of ventricular pacing by signal generation circuitry within the housing of the pacing device based on the determination.

* * * * *